US012383213B2

(12) United States Patent
Horiuchi et al.

(10) Patent No.: US 12,383,213 B2
(45) Date of Patent: Aug. 12, 2025

(54) RADIOGRAPHY SYSTEM

(71) Applicant: FUJIFILM CORPORATION, Tokyo (JP)

(72) Inventors: Hisatsugu Horiuchi, Kanagawa (JP); Yuji Kai, Kanagawa (JP); Yuji Jibiki, Kanagawa (JP); Koji Taninai, Kanagawa (JP); Masataka Sugahara, Kanagawa (JP); Takeyasu Kobayashi, Kanagawa (JP); Naoyuki Nishino, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 360 days.

(21) Appl. No.: 18/059,985

(22) Filed: Nov. 30, 2022

(65) Prior Publication Data

US 2023/0225686 A1 Jul. 20, 2023

(30) Foreign Application Priority Data

Jan. 18, 2022 (JP) ................. 2022-005637

(51) Int. Cl.
*A61B 6/00* (2024.01)
*A61B 6/42* (2024.01)

(52) U.S. Cl.
CPC .......... *A61B 6/4405* (2013.01); *A61B 6/4225* (2013.01); *A61B 6/4283* (2013.01); *A61B 6/547* (2013.01)

(58) Field of Classification Search
CPC ..... A61B 6/4452; A61B 6/4283; A61B 6/587; A61B 6/4225; A61B 6/547; A61B 6/4405; A61B 6/4233; A61B 6/461; A61B 6/5294; A61B 6/4208; A61B 6/44; A61B 6/4085; A61B 6/542; A61B 6/464; A61B 6/545; A61B 5/7264; A61B 6/589; A61B 6/08; A61B 6/465; A61B 5/4887; A61B 6/04;

(Continued)

(56) References Cited

U.S. PATENT DOCUMENTS 6,592,259 B2 * 7/2003 Crain ................... A61B 6/4458
378/197
7,798,710 B1 * 9/2010 Barnes ................... A61B 6/587
378/197

(Continued)

FOREIGN PATENT DOCUMENTS

JP 5735725 B2 6/2015

*Primary Examiner* — Irakli Kiknadze
(74) *Attorney, Agent, or Firm* — SOLARIS Intellectual Property Group, PLLC

(57) ABSTRACT

A radiography system includes a radiation source that emits radiation, an electronic cassette that receives the radiation and detects a radiographic image, a portable first retainer that holds the electronic cassette, a string that is attached to the first retainer, and a camera that images the string. The first retainer includes a lock portion and a movable portion as an inclination change mechanism that can change an inclination of the electronic cassette with respect to the radiation source. The string and the camera constitute a first detection mechanism that detects an inclination of the electronic cassette about an X-axis which intersects a Z-axis and is directed toward the radiation source in a case in which a radiation detection surface of the electronic cassette and the radiation source are disposed to face each other.

14 Claims, 21 Drawing Sheets

(58) Field of Classification Search
CPC ..... A61B 5/0077; A61B 6/4411; A61B 6/467; A61B 6/463; A61B 6/42; A61B 6/50; A61B 5/0035; A61B 5/743; A61B 5/748; A61B 6/54; A61B 6/544; A61B 5/744; A61B 6/588; A61B 2562/0223; A61B 6/40; A61B 6/5247; A61B 6/4464; A61B 6/06; A61B 6/4441; A61B 6/487; A61B 6/488; A61B 6/4291; A61B 6/4028; A61B 6/4458; A61B 6/102; A61B 6/4014; A61B 6/4266; A61B 6/032; A61B 6/486; A61B 6/5235; A61B 6/4476; A61B 6/4007; A61B 6/4435; A61B 2034/2065; A61B 6/5264; A61B 6/466; A61B 8/5276; A61B 6/469; A61B 6/0407; A61B 6/56; A61B 2562/0219; A61B 6/00; A61B 2576/02; A61B 5/6886; A61B 6/5217; G01T 7/00; G01T 1/17; G01B 15/02; G21K 1/04; G21K 1/025; G06T 7/74; G06T 2207/10048; G06T 2207/20081; G06T 2207/20084; G06T 2207/30204; G06T 7/0012; G06T 2207/10116; A61N 5/1067; A61N 5/1049; A61N 5/1083; A61N 5/1037; A61N 2005/1061; A61N 2005/1072; A61N 2005/1054; A61N 5/1081; G02B 30/54; B25J 9/04; H05H 9/00; G16H 30/20; G16H 30/40; G16H 50/70; G16H 50/20; G16H 50/30; G06V 10/143; G06V 10/25; G06V 10/803; H04N 23/30; H04N 23/95; H04N 23/80; G06F 18/251

USPC .................................................. 378/198, 205

See application file for complete search history.

(56) References Cited

U.S. PATENT DOCUMENTS

| 9,649,074 | B2* | 5/2017 | Simon | ................... A61B 6/4405 |
|---|---|---|---|---|
| 9,795,021 | B2* | 10/2017 | Ye | ............................. H05G 1/02 |
| 2004/0017887 | A1* | 1/2004 | Le | ............................. G01V 5/20 378/57 |
| 2008/0240343 | A1 | 10/2008 | Jabri et al. | |
| 2022/0183650 | A1* | 6/2022 | Saito | .................... A61B 6/4283 |

* cited by examiner

RADIOGRAPHY SYSTEM

CROSS-REFERENCE TO RELATED APPLICATIONS

The present application claims priority under 35 U.S.C. § 119 to Japanese Patent Application No. 2022-005637, filed on Jan. 18, 2022. The above application is hereby expressly incorporated by reference, in its entirety, into the present application.

BACKGROUND

1. Technical Field

The technology of the present disclosure relates to a radiography system.

2. Description of the Related Art

A radiography system has been proposed which can perform radiography not only in a limited environment, such as a medical facility, but also in a special environment, such as the site of an accident, the site of a disaster, or a camp in a conflict area. For example, JP5735725B discloses a radiography system including a radiation source that emits radiation, a radiographic image detector that receives the radiation and detects a radiographic image, a tripod that holds the radiation source, and a tripod that holds the radiographic image detector.

The radiography system disclosed in JP5735725B is provided with a sensor that detects the relative positions of the radiation source and the radiographic image detector (referred to as an "orientation sensor", an "orientation transceiver", or the like in JP5735725B) in preparation for a case in which the radiation source and the radiographic image detector are installed in a special environment and the relative positions thereof deviate from each other. In JP5735725B, it is possible to adjust the relative positions of the radiation source and the radiographic image detector on the basis of the output of this sensor.

SUMMARY

In the radiography system disclosed in JP5735725B, the relative positions of the radiation source and the radiographic image detector are detected by the sensor. However, the inclination of the radiographic image detector about a first axis is not detected. Here, the first axis is an axis that intersects a vertical axis and is directed to the radiation source in a case in which a radiation detection surface of the radiographic image detector and the radiation source are disposed to face each other.

In JP5735725B, as described above, the inclination of the radiographic image detector about the first axis is not detected. Therefore, there is a concern that, in a state in which the radiographic image detector is inclined about the first axis, radiography will be performed on a subject in a posture in which a craniocaudal axis is parallel to the vertical axis and a radiographic image in which the subject is obliquely captured will be detected, resulting in a failure in radiography. In particular, in many cases, the installation surface is uneven in a special environment such as the site of an accident, the site of a disaster, or a camp in a conflict area, and the radiographic image detector is likely to be inclined about the first axis. Therefore, there is an increasing concern that radiography will fail due to the performance of the radiography in a state in which the radiographic image detector is inclined about the first axis.

One embodiment according to the technology of the present disclosure provides a radiography system that can reduce a concern that radiography will fail due to the performance of the radiography in a state in which a radiographic image detector is inclined about a first axis.

According to an aspect of the present disclosure, there is provided a radiography system comprising: a radiation source that emits radiation; a radiographic image detector that receives the radiation and detects a radiographic image; a portable retainer that holds the radiographic image detector and includes an inclination change mechanism which is capable of changing an inclination of the radiographic image detector with respect to the radiation source; and a first detection mechanism that detects an inclination of the radiographic image detector about a first axis which intersects a vertical axis and which is directed toward the radiation source in a case in which a detection surface for the radiation in the radiographic image detector and the radiation source are disposed to face each other.

Preferably, the radiography system further comprises a first processor, and the first processor performs control to display the inclination of the radiographic image detector about the first axis on a display.

Preferably, the first processor calculates an amount of displacement of the inclination change mechanism for reducing deviation of the inclination of the radiographic image detector about the first axis on the basis of the inclination of the radiographic image detector about the first axis and performs control to display the calculated amount of displacement on the display.

Preferably, the first detection mechanism includes a string that hangs down in a direction parallel to the vertical axis and a first camera that images the string, and the first processor analyzes an image including the string captured by the first camera to detect the inclination of the radiographic image detector about the first axis.

Preferably, the first camera is provided in the radiation source.

Preferably, the first detection mechanism includes an acceleration sensor, and the first processor detects the inclination of the radiographic image detector about the first axis on the basis of a measurement result of the acceleration sensor.

Preferably, the radiography system further comprises a second detection mechanism that detects an inclination of the radiographic image detector about at least one of the vertical axis or a second axis which intersects the vertical axis and the first axis.

Preferably, the radiography system further comprises a second processor. The second processor performs control to display the inclination of the radiographic image detector about the at least one of the vertical axis or the second axis on a display.

Preferably, the second processor calculates an amount of displacement of the inclination change mechanism for reducing deviation of the inclination of the radiographic image detector about the at least one of the vertical axis or the second axis on the basis of the inclination of the radiographic image detector about the at least one of the vertical axis or the second axis and performs control to display the calculated amount of displacement on the display.

Preferably, the second detection mechanism includes at least three markers that are provided in the radiographic image detector or the retainer and a second camera that images the markers, and the second processor analyzes an image captured by the second camera to detect the inclination of the radiographic image detector about the at least one of the vertical axis or the second axis.

Preferably, the second processor analyzes the image captured by the second camera to further detect a distance from a generation point of the radiation to the detection surface of the radiographic image detector and a position of the radiographic image detector with respect to an irradiation center of the radiation in a plane configured by the vertical axis and the second axis.

Preferably, the second camera is provided in the radiation source.

Preferably, the retainer includes a holder to which the radiographic image detector is attached and at least three leg portions that support the holder.

Preferably, in a case in which the second detection mechanism includes the markers, the markers are provided in the holder.

Preferably, the retainer includes a fixing mechanism that fixes a positional relationship between the holder and the leg portions.

According to the technology of the present disclosure, it is possible to provide a radiography system which can reduce a concern that radiography will fail due to the performance of the radiography in a state in which a radiographic image detector is inclined about a first axis.

BRIEF DESCRIPTION OF THE DRAWINGS

Exemplary embodiments according to the technique of the present disclosure will be described in detail based on the following figures, wherein.

DETAILED DESCRIPTION

Hereinafter, an example of an embodiment of the technology of the present disclosure will be described with reference to the drawings. In addition, the terms "first" and "second" used in the specification are added to avoid confusion of components and do not limit the number of components present in a radiography system.

First Embodiment

Figure 1:
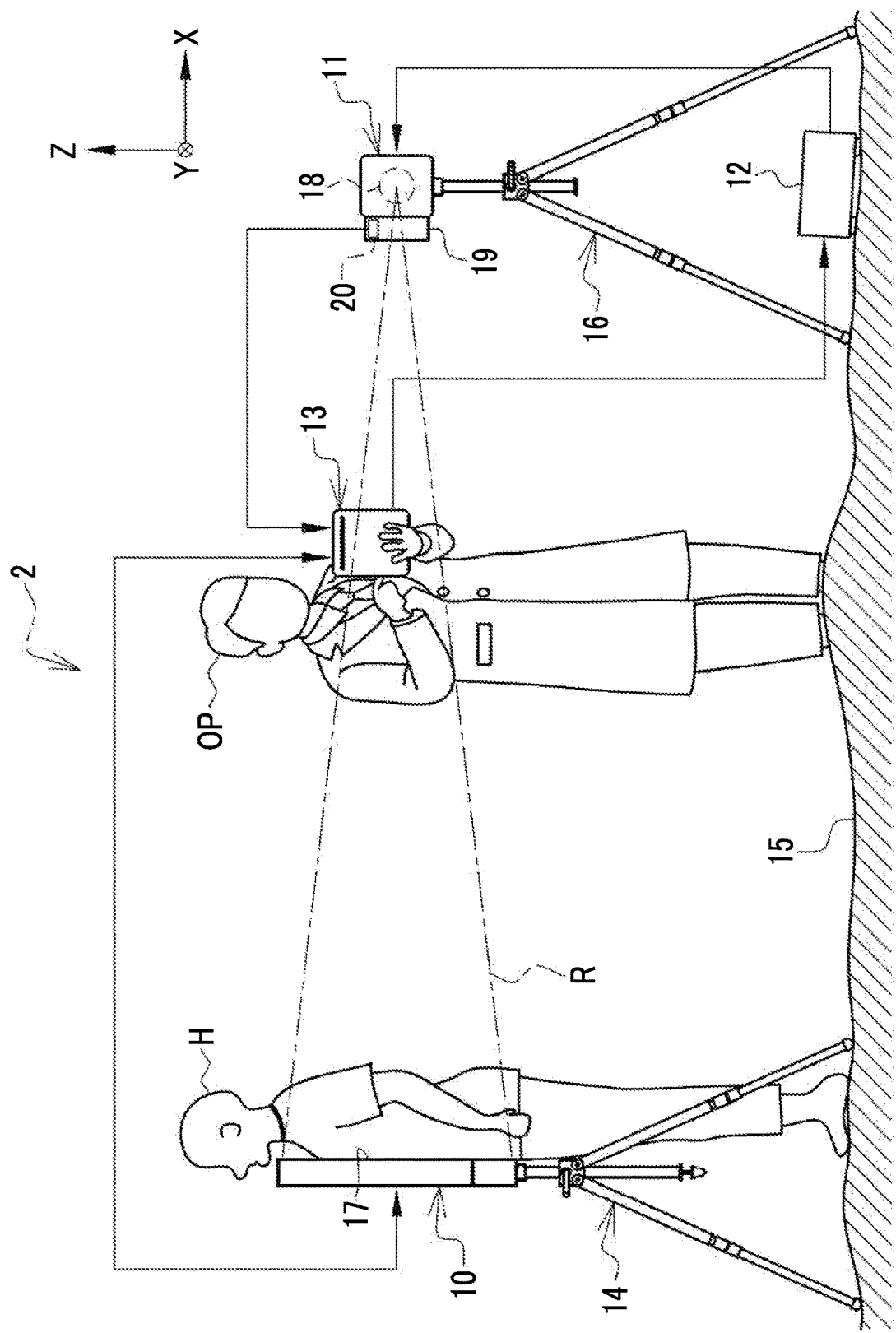
FIG. 1 is a diagram illustrating a radiography system.

For example, as illustrated in FIG. 1, a radiography system 2 is a system that captures a radiographic image of a subject H using radiation R such as X-rays or γ-rays. The radiography system 2 includes, for example, an electronic cassette 10, a radiation source 11, a radiation source control device 12, and a console 13. The electronic cassette 10 is held by a portable first retainer 14 and is disposed on an installation surface 15 at an imaging site through the first retainer 14. The radiation source 11 is also held by a portable second retainer 16 and is disposed on the installation surface 15 at the imaging site through the second retainer 16. The radiation source control device 12 is directly placed on the installation surface 15. The imaging site illustrated in FIG. 1 is an imaging site in a special environment, such as the site of an accident or disaster or a camp in a conflict area. The installation surface 15 is uneven.

The electronic cassette 10 is a portable radiographic image detector that outputs a radiographic image corresponding to the radiation R transmitted through the subject H. The electronic cassette 10 is disposed such that a detection surface 17 for the radiation R faces the radiation source 11. The electronic cassette 10 is connected to the console 13 such that it can communicate with the console 13 wirelessly or in a wired manner. In addition, the electronic cassette 10 is an example of a "radiographic image detector" according to the technology of the present disclosure. Further, in the following description, a vertical axis is referred to as a Z-axis, a first axis which intersects the Z-axis and is directed toward the radiation source 11 in a case in which the detection surface 17 of the electronic cassette 10 and the radiation source 11 are disposed to face each other is referred to as an X-axis, and a second axis which intersects the Z-axis and the X-axis is referred to as a Y-axis. Specifically, the X-axis is a horizontal axis orthogonal to the Z-axis, and the Y-axis is a horizontal axis orthogonal to the Z-axis and the X-axis. Here, the terms "orthogonal" and "horizontal" indicate orthogonal and horizontal including an error (for example, an error of about 1% to 10%), which is generally allowed in the technical field to which the technology of the present disclosure belongs and is not contrary to the gist of the technology of the present disclosure, in addition to perfectly orthogonal and perfectly horizontal. Similarly, the term indicating an angle of "30°", which will be described below, includes an error (for example, an error of about 1% to 10%) which is generally allowed in the technical field to which the technology of the present disclosure belongs and is not contrary to the gist of the technology of the present disclosure.

The electronic cassette 10 has a detection panel in which a plurality of pixels accumulating charge corresponding to the radiation R are arranged in a two-dimensional matrix. The detection panel is also called a flat panel detector (FPD). The electronic cassette 10 has a function of detecting the start and end of the emission of the radiation R. In a case in which the start of the emission of the radiation R is detected, the detection panel starts an accumulation operation of accumulating charge in the pixels. In a case in which the end of the emission of the radiation R is detected, the detection panel starts a reading operation of reading the charge accumulated in the pixels as an electric signal.

In addition, the electronic cassette 10 and the radiation source control device 12 may be connected such that they can communicate with each other, and synchronizing signals indicating the start and end of the emission of the radiation R may be exchanged between the electronic cassette 10 and the radiation source control device 12 to synchronize the emission start timing of the radiation R and the start timing of the accumulation operation and to synchronize the emission end timing of the radiation R and the start timing of the reading operation.

The console 13 is a tablet terminal and is carried by an operator OP such as a radiology technician. The console 13 has a touch panel display 55 (see FIG. 4) that displays various screens and receives an operation instruction from the operator OP. The touch panel display 55 is an example of a "display" according to the technology of the present disclosure. The console 13 transmits various signals to the electronic cassette 10. In addition, the console 13 receives a radiographic image from the electronic cassette 10. The console 13 displays the radiographic image on the touch panel display 55. The console 13 may be a notebook personal computer.

The console 13 receives an instruction to select an imaging menu for radiography from the operator OP. The imaging menu is a combination of an imaging part, such as the chest or the abdomen, an imaging posture, such as a standing posture or a sitting posture, and an imaging orientation, such as the front, the back, and the side. A source-to-image receptor distance (SID), which is a distance from a generation point of the radiation R to the detection surface 17 of the electronic cassette 10, is associated with the imaging menu.

The radiation source 11 has a radiation tube 18 and an irradiation field limiter 19. The radiation tube 18 is provided with, for example, a filament, a target, and a grid electrode (none of which are illustrated). A voltage is applied between the filament, which is a cathode, and the target, which is an anode. The voltage applied between the filament and the target is called a tube voltage. The filament emits thermoelectrons corresponding to the applied tube voltage to the target. The target emits the radiation R by the collision of the thermoelectrons from the filament. The grid electrode is disposed between the filament and the target. The grid electrode changes the flow rate of the thermoelectrons from the filament to the target according to the applied voltage. The flow rate of the thermoelectrons from the filament to the target is called a tube current. In addition, the above-mentioned generation point of the radiation R is a point at which the thermoelectron collides with the target.

The irradiation field limiter 19 is also called a collimator and limits an irradiation field of the radiation R emitted from the radiation tube 18. For example, the irradiation field limiter 19 has a configuration in which four shielding plates made of lead or the like that shields the radiation R are disposed on each side of a quadrangle and a quadrangular emission opening for transmitting the radiation R is formed in a central portion. The irradiation field limiter 19 changes the position of each shielding plate to change the size of the emission opening, thereby changing the irradiation field of the radiation R. In addition, in this example, the radiation source 11 is used as a reference for adjusting the position and the posture, and the adjustment of the inclinations of the radiation source 11 about the Y-axis and the Z-axis is unnecessary. Therefore, the emission opening of the irradiation field limiter 19 is always set to the maximum size, and the irradiation field of the radiation R is also always set to the maximum size.

A camera 20 is provided in the irradiation field limiter 19. The camera 20 is a digital camera that captures a digital image. The camera 20 is connected to the console 13 such that it can communicate with the console 13 wirelessly or in a wired manner. The camera 20 images portions of the electronic cassette 10 and the first retainer 14 in response to an imaging instruction from the console 13. The camera 20 transmits a captured image 75 (see FIG. 5 and the like) obtained by imaging portions of the electronic cassette 10 and the first retainer 14 to the console 13. For example, the disposition of the camera 20 is adjusted such that a line LC (see FIG. 14), which passes through the center (the center of the angle of view) of the captured image 75 and is parallel to the Z-axis, is matched with a line which passes through the irradiation center of the radiation R and is parallel to the Z-axis. The irradiation center of the radiation R is the center of the irradiation field of the radiation R which is defined by the irradiation field limiter 19. The camera 20 is an example of a "first camera" and a "second camera" according to the technology of the present disclosure.

The instruction to capture the captured image 75 is issued to the camera 20 through the console 13 a total of three times. A first imaging instruction is issued in a case in which the electronic cassette 10 and the radiation source 11 are first installed on the installation surface 15 through the first retainer 14 and the second retainer 16. A second imaging instruction is issued after the deviation of the inclination of the electronic cassette 10 about the X-axis is reduced on the basis of the captured image 75 captured by the first imaging instruction. A third imaging instruction is issued after the deviation of the inclinations of the electronic cassette 10 about the Y-axis and the Z-axis is reduced on the basis of the captured image 75 captured by the second imaging instruction.

The radiation source 11 is connected to the radiation source control device 12 in a wired manner. In addition, the console 13 is connected to the radiation source control device 12 such that it can communicate with the radiation source control device 12 wirelessly or in a wired manner. The radiation source control device 12 controls the operation of the radiation source 11 in response to various operation instructions from the console 13.

The operator OP sets the irradiation conditions of the radiation R in the radiation source control device 12 through the console 13. The irradiation conditions are a tube voltage applied to the radiation tube 18, a tube current, and an irradiation time of the radiation R. Approximate values of the irradiation conditions are predetermined by the imaging menu. In addition, the operator OP inputs an instruction to start the emission of the radiation R to the radiation source control device 12 through the console 13. In a case in which the irradiation start instruction is input from the console 13, the radiation source control device 12 directs the radiation tube 18 to emit the radiation R under the set irradiation conditions. In a case in which the irradiation time set in the irradiation conditions has elapsed since the start of the emission of the radiation R, the radiation source control device 12 stops the emission of the radiation R from the radiation tube 18. In addition, the emission of the radiation R may be ended by an auto exposure control (AEC) function. The AEC function is a function that detects the dose of the radiation R during the emission of the radiation R and stops the emission of the radiation R from the radiation tube 18 at the time when an integrated value of the detected dose (cumulative dose) reaches a preset target dose. In this case, the detection panel of the electronic cassette 10 starts the reading operation in a case in which the cumulative dose of the radiation R reaches the target dose. In addition, the irradiation condition may be a tube current-irradiation time product which is a product of the tube current and the irradiation time.

Figure 2:
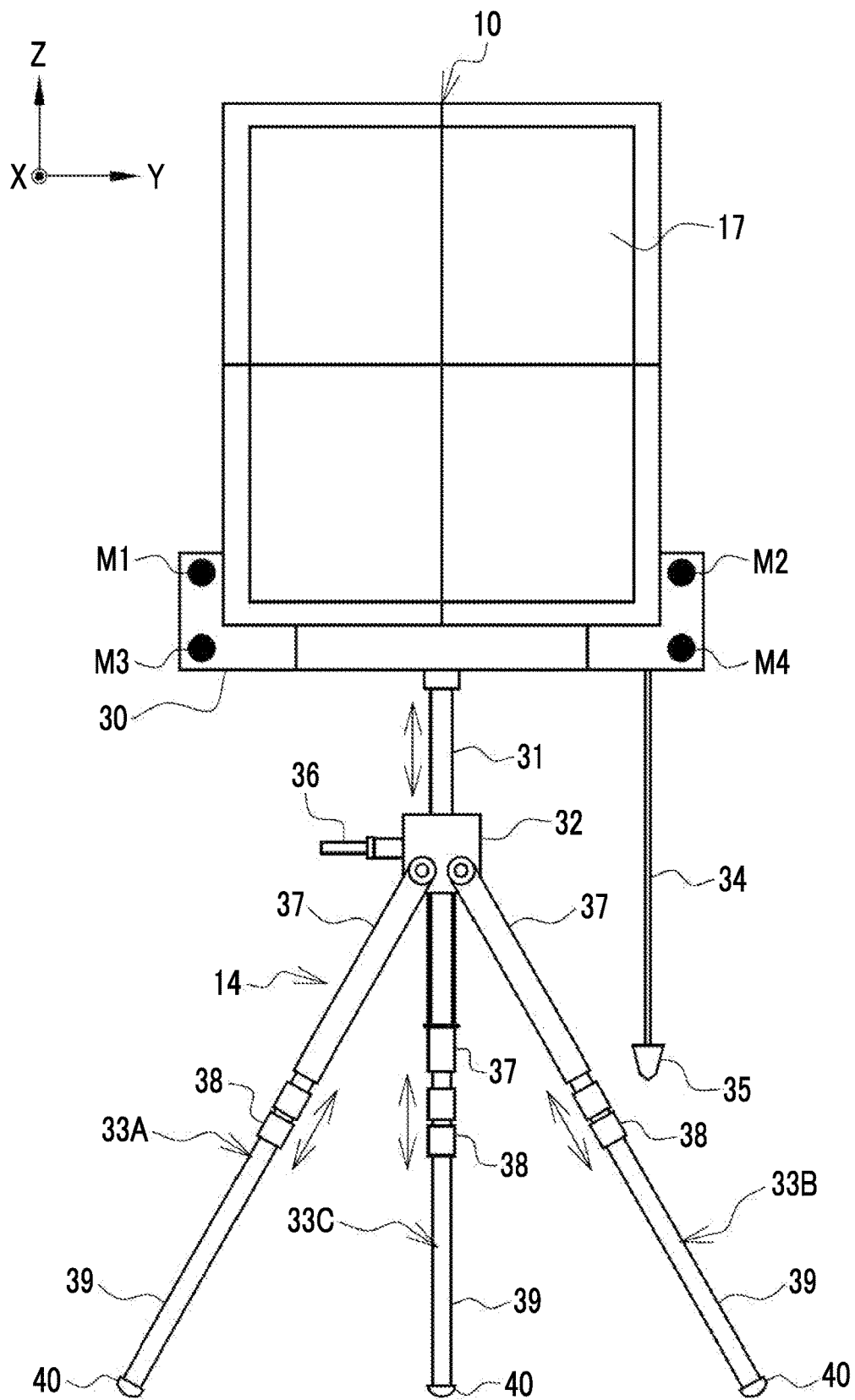
FIG. 2 is a diagram illustrating an electronic cassette and a first retainer.

For example, as illustrated in FIG. 2, the first retainer 14 is a so-called tripod having, for example, a holder 30, a center pole 31, a main body portion 32, and three leg portions 33A, 33B, 33C. The electronic cassette 10 is attachably and detachably attached to the holder 30. The first retainer 14 is an example of a "retainer" according to the technology of the present disclosure. Further, in the following description, in a case in which the leg portions 33A to 33C do not need to be particularly distinguished from each other, they may be collectively referred to as leg portions 33.

One end of a string 34 is attached to a lower right portion of the holder 30. A weight 35 is attached to the other end of the string 34. The string 34 hangs down in a direction parallel to the Z-axis without loosening by the action of the weight 35. The string 34 may be any object as long as it hangs down in the direction parallel to the Z-axis without loosening. However, it is preferable that the string 34 is made of a material that shields the radiation R in order to facilitate the extraction of an image of the string 34 from the captured image 75. For example, the string 34 is a lead wire or chain having a thickness of several millimeters and a length of several tens of centimeters. The string 34 is provided to detect the inclination of the electronic cassette 10 about the X-axis with respect to the radiation source 11. The string 34 and the camera 20 constitute a "first detection mechanism" according to the technology of the present disclosure.

Four markers M1, M2, M3, and M4 are provided on a surface of the holder 30 that is on the side on which the detection surface 17 of the electronic cassette 10 is disposed. The marker M1 is disposed at an upper left corner, the marker M2 is disposed at an upper right corner, the marker M3 is disposed at a lower left corner, and the marker M4 is disposed at a lower right corner. Similarly to the string 34, it is preferable that the markers M1 to M4 are made of a material that shields the radiation R in order to facilitate the extraction of an image of the markers M1 to M4 from the captured image 75. For example, the markers M1 to M4 are circular lead plates having a diameter of about several centimeters. The markers M1 to M4 are provided to detect the inclinations of the electronic cassette 10 about the Y-axis and the Z-axis with respect to the radiation source 11. The markers M1 to M4 and the camera 20 constitute a "second detection mechanism" according to the technology of the present disclosure.

The markers M1 to M4 are disposed at positions where a figure formed by lines connecting the centers of the markers M1 to M4 is a rectangle in a case in which there is no deviation in the inclination of the electronic cassette 10 with respect to the radiation source 11 about any of the X-axis, the Y-axis, or the Z-axis. That is, the marker M1 and the marker M2 are provided at the same height position with respect to the Z-axis. Similarly, the marker M3 and the marker M4 are provided at the same height position with respect to the Z-axis. Further, the marker M1 and the marker M3 are provided at the same horizontal position with respect to the Y-axis. Similarly, the marker M2 and the marker M4 are provided at the same horizontal position with respect to the Y-axis.

One end of the center pole 31 is connected to the holder 30, and the other end of the center pole 31 penetrates the main body portion 32 and extends downward. The center pole 31 is connected to a handle 36 by a worm gear consisting of a cylindrical worm and a worm wheel or a rack and pinion gear in the main body portion 32 and can be move up and down in the direction of an arrow with respect to the main body portion 32 by rotating the handle 36. The height position of the holder 30 and thus the electronic cassette 10 can be adjusted by the vertical movement of the center pole 31. Graduations are provided on the center pole 31 at intervals of, for example, 1 cm such that the height position of the electronic cassette 10 can be known.

The leg portions 33A to 33C have the same configuration and have a base portion 37, a lock portion 38, a movable portion 39, and a ferrule 40 in this order from the main body portion 32. The base portions 37 are connected to the main body portions 32 at intervals of 120° and can be opened and closed with respect to the main body portions 32. The lock portion 38 is, for example, a lock nut that is loosened in a case in which it is turned counterclockwise and is tightened in a case in which it is turned clockwise. The movable portion 39 can be expanded and contracted in the direction of the arrow with respect to the base portion 37 in a case in which the lock portion 38 is loosened. Graduations are provided on the movable portion 39, for example, at intervals of 1 cm such that the amount of expansion and contraction (the amount of displacement) with respect to the base portion 37 can be known. The ferrule 40 is a portion that comes into direct contact with the installation surface 15. The lock portion 38 and the movable portion 39 are an example of an "inclination change mechanism" according to the technology of the present disclosure. In addition, the lock portion 38 may be a lock lever that has two positions of a lock position and a lock release position.

Figure 3:
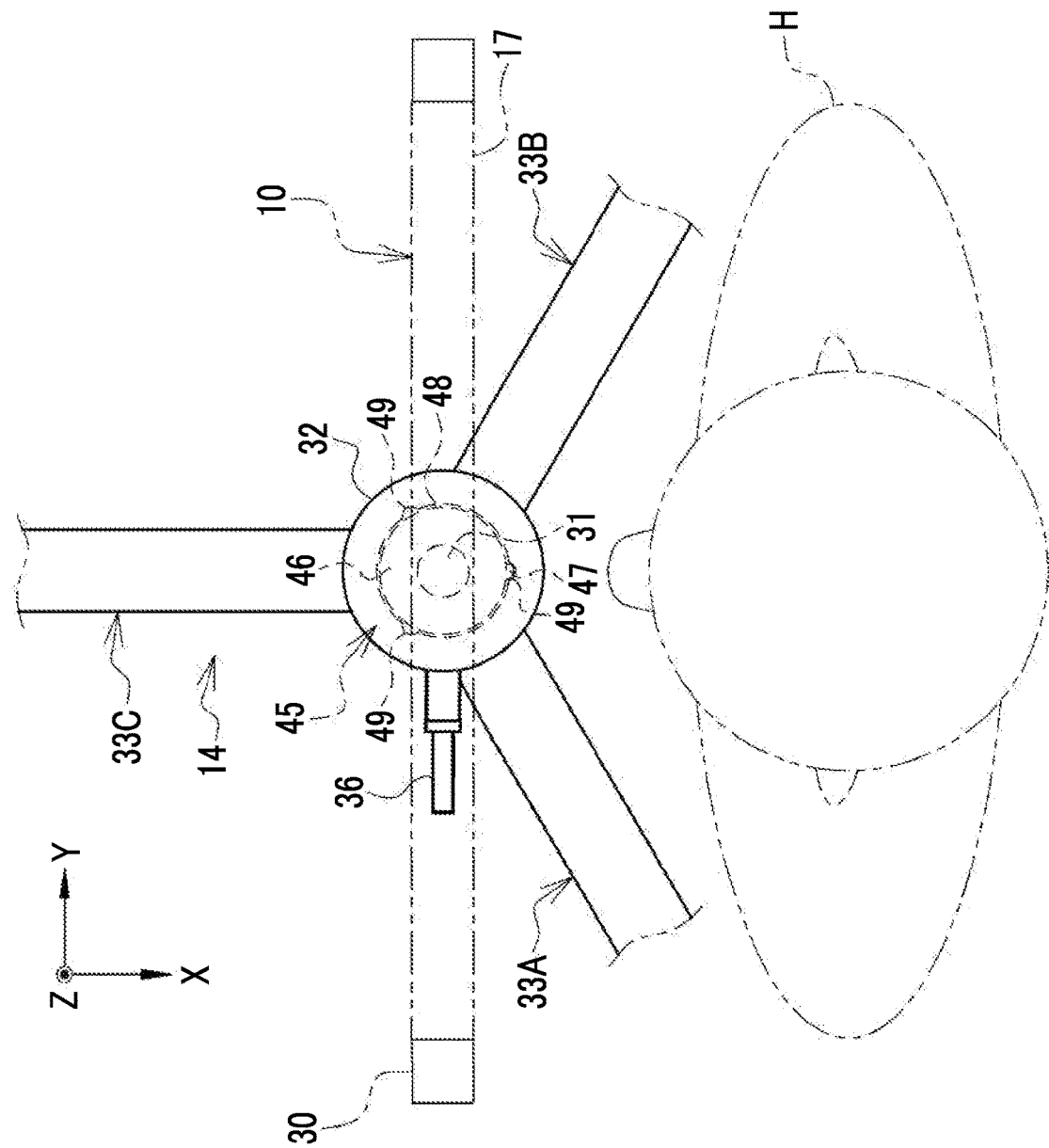
FIG. 3 is a plan view illustrating the first retainer as viewed from a Z-axis direction.

For example, as illustrated in FIG. 3, the main body portion 32 is provided with a fixing mechanism 45 for fixing the positional relationship between the holder 30 and the leg portions 33. The fixing mechanism 45 is a click stop mechanism including a holding portion 46 that holds the center pole 31 therein to be movable up and down, a click ball 47 that can project from and retract into the holding portion 46, and a rotating portion 48 that is rotated about the holding portion 46 using the center pole 31 as an axis. The rotating portion 48 can be rotated to change the positions of the leg portions 33A to 33C. Graduations are provided on the main body portion 32 at intervals of, for example, 1° such that it is possible to know how many degrees the main body portion 32 has been rotated from the original position.

Grooves 49 into which the click ball 47 is fitted are formed in the rotating portion 48 at intervals of 120°. In the case of FIG. 3 which is a plan view of the first retainer 14, to which the electronic cassette 10 is attached, as seen from the Z-axis direction, the groove 49 is formed at the position where one leg portion 33 (in FIG. 3, any one of the leg portion 33C, the leg portion 33A, or the leg portion 33B) among the leg portions 33A to 33C and the detection surface 17 of the electronic cassette 10 are orthogonal to each other. In addition, in the case of FIG. 3 which is a plan view of the first retainer 14, to which the electronic cassette 10 is attached, as seen from the Z-axis direction, the grooves 49 are provided at positions where two adjacent leg portions 33 (in FIG. 3, any of the leg portions 33A and 33B, the leg portions 33B and 33C, or the leg portions 33C and 33A) other than the leg portion 33 at the position orthogonal to the detection surface 17 of the electronic cassette 10 extend in directions that are symmetric with respect to the detection surface 17 of the electronic cassette 10, specifically, in directions having an angle of 30° from the detection surface 17. The positional relationship between the holder 30 and the leg portions 33A to 33C is always fixed to the above-described state by forming the grooves 49 at these positions. In addition, the second retainer 16 has the same basic configuration as the first retainer 14 except that the object to be held is changed from the electronic cassette 10 to the radiation source 11. Therefore, the description thereof will not be repeated.

Figure 4:
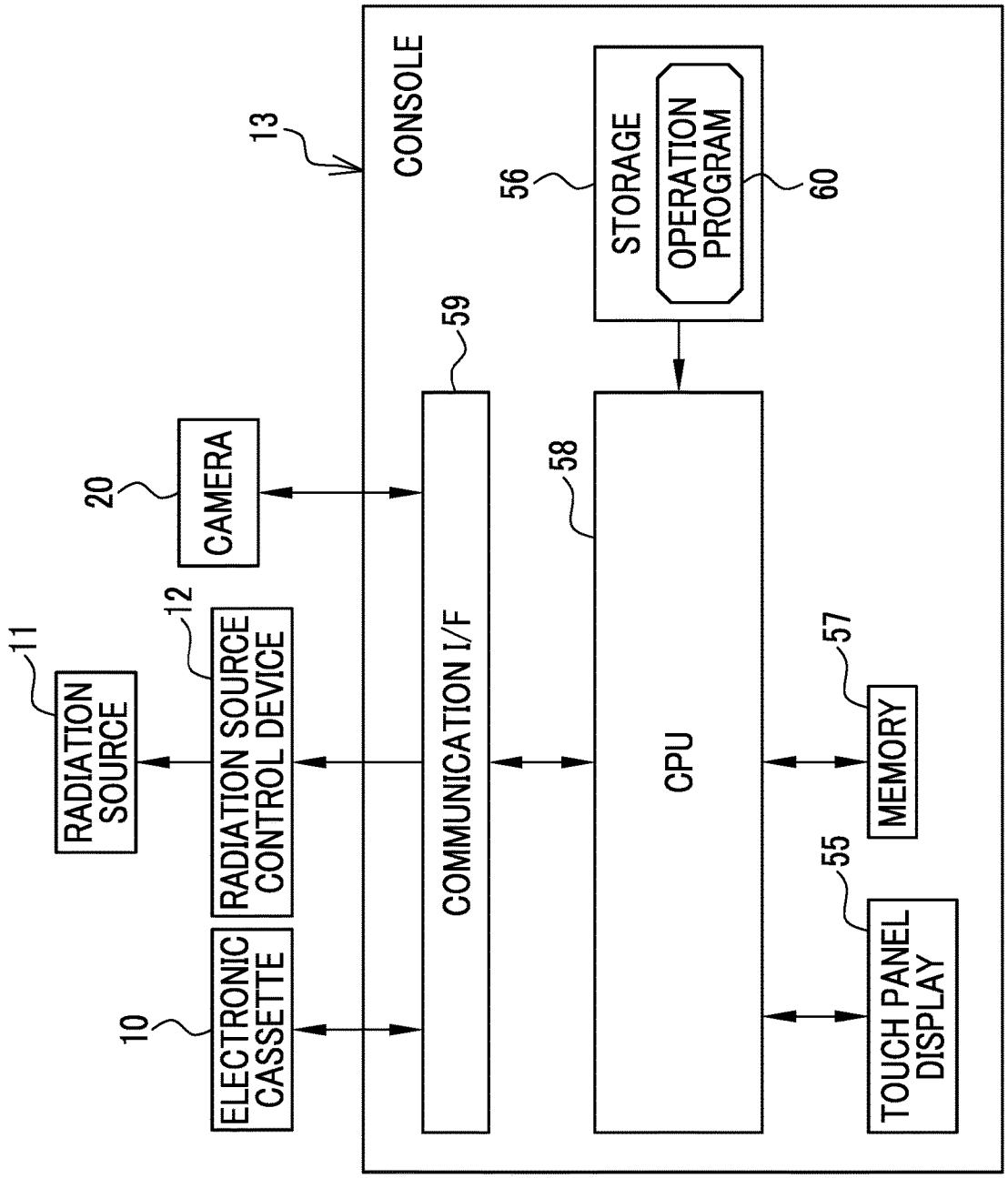
FIG. 4 is a block diagram illustrating an internal configuration of a console.

For example, as illustrated in FIG. 4, the console 13 comprises a storage 56, a memory 57, a central processing unit (CPU) 58, and a communication interface (I/F) 59 in addition to the touch panel display 55. The touch panel display 55, the storage 56, the memory 57, the CPU 58, and the communication I/F 59 are connected to each other through a bus line (not illustrated).

The storage 56 is a hard disk drive that is provided in the computer constituting the console 13 or is connected to the computer through a cable or a network. The storage 56 stores, for example, a control program, such as an operating system, various application programs including an operation program 60, and various kinds of data associated with these programs. The operation program 60 is an application program for causing the computer to function as the console 13. In addition, a solid state drive may be used instead of the hard disk drive.

The memory 57 is a work memory used by the CPU 58 to perform processes. The CPU 58 loads the program stored in the storage 56 to the memory 57 and performs a process corresponding to the program. Therefore, the CPU 58 controls the overall operation of each unit of the computer. The CPU 58 is an example of a "first processor" and a "second processor" according to the technology of the present disclosure. In addition, the memory 57 may be provided in the CPU 58. The communication I/F 59 controls the transmission of various kinds of information to external devices such as the electronic cassette 10, the radiation source control device 12, and the camera 20.

Figure 5:
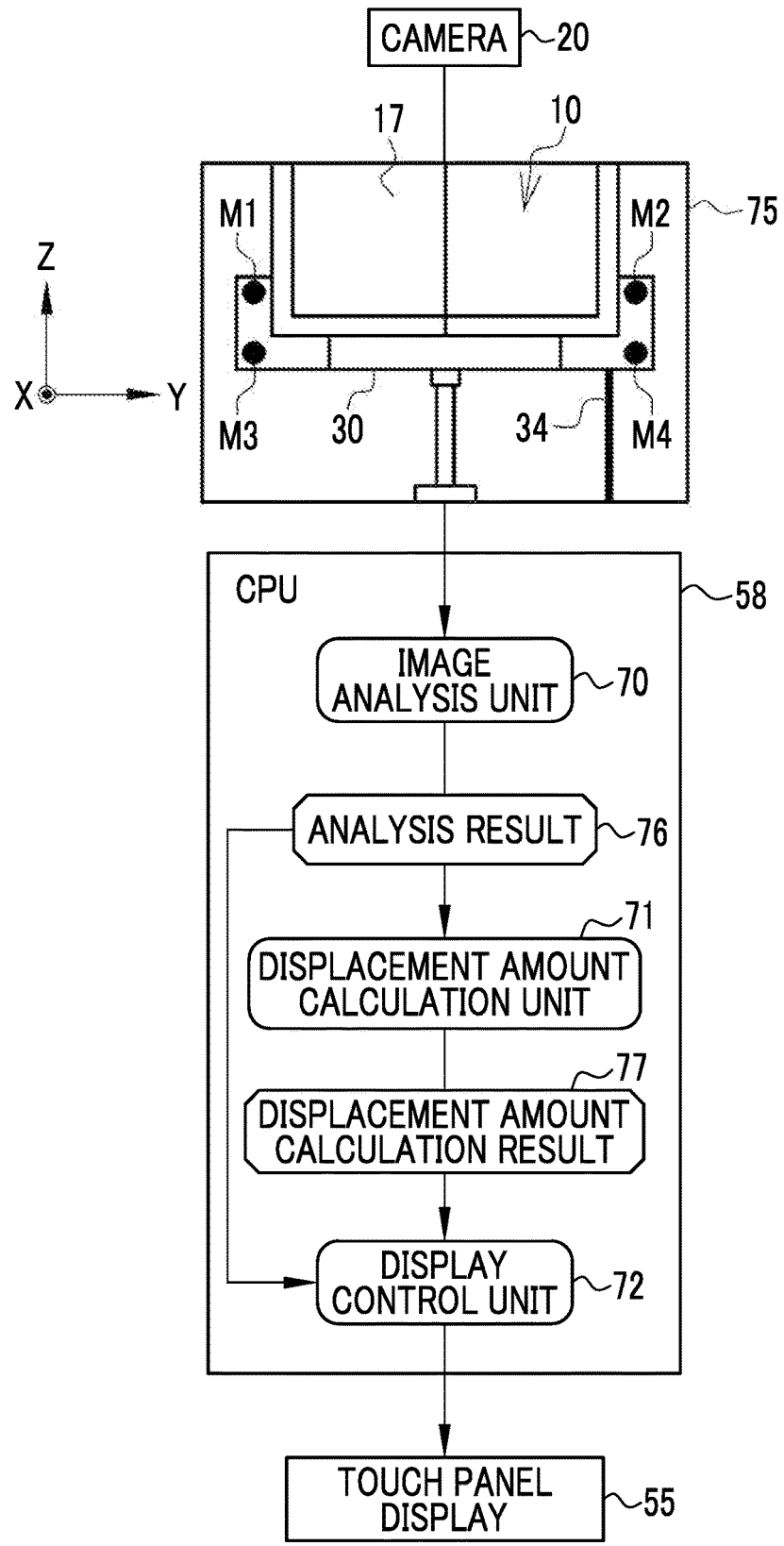
FIG. 5 is a diagram illustrating an image captured by a camera and a processing unit of a CPU of the console.

For example, as illustrated in FIG. 5, in a case in which the operation program 60 is started, the CPU 58 of the computer constituting the console 13 functions as an image analysis unit 70, a displacement amount calculation unit 71, and a display control unit 72 in cooperation with the memory 57 and the like.

The captured image 75 from the camera 20 is input to the image analysis unit 70. The captured image 75 includes, for example, a lower portion of the electronic cassette 10, the holder 30, and the string 34. The image analysis unit 70 analyzes the captured image 75 to detect the inclinations of the electronic cassette 10 about the X-axis, the Y-axis, and the Z-axis. In addition, the image analysis unit 70 analyzes the captured image 75 to detect the SID and the position of the electronic cassette 10 with respect to the irradiation center of the radiation R in a YZ plane configured by the Y-axis and the Z-axis (hereinafter, simply referred to as a position with respect to the irradiation center). The image analysis unit 70 outputs, for example, the detected inclinations of the electronic cassette 10 as an analysis result 76 to the displacement amount calculation unit 71 and the display control unit 72.

The displacement amount calculation unit 71 calculates the amount of displacement of the movable portion 39 for reducing the deviation of the inclination of the electronic cassette 10 about the X-axis on the basis of the inclination of the electronic cassette 10 about the X-axis in the analysis result 76. In addition, the displacement amount calculation unit 71 calculates the amount of displacement of the movable portion 39 for reducing the deviation of the inclination of the electronic cassette 10 about the Y-axis on the basis of the inclination of the electronic cassette 10 about the Y-axis in the analysis result 76. The displacement amount calculation unit 71 outputs a displacement amount calculation result 77 to the display control unit 72. Here, the amount of displacement of the movable portion 39 for reducing the deviation of the inclination of the electronic cassette 10 is, for example, the amount of displacement for eliminating the deviation. The amount of displacement for eliminating the deviation may include not only the amount of displacement for completely eliminating the deviation but also an error (for example, an error of about 1% to 10%) that is generally allowed in the technical field to which the technology of the present disclosure belongs and is not contrary to the gist of the technology of the present disclosure. Alternatively, the amount of displacement of the movable portion 39 for reducing the deviation of the inclination of the electronic cassette 10 may be the amount of displacement for making the deviation less than a preset threshold value.

The display control unit 72 performs control to display various screens on the touch panel display 55. For example, the display control unit 72 performs control to display a first notification screen 90 (see FIG. 8) including the inclination of the electronic cassette 10 about the X-axis and the amount of displacement of the movable portion 39 for reducing the deviation of the inclination of the electronic cassette 10 about the X-axis on the touch panel display 55. In addition, the display control unit 72 performs control to display a second notification screen 115 (see FIG. 12) including the inclinations of the electronic cassette 10 about the Y-axis and the Z-axis and the amount of displacement of the movable portion 39 for reducing the deviation of the inclinations of the electronic cassette 10 about the Y-axis on the touch panel display 55. Further, the display control unit 72 performs control to display a third notification screen 125 (see FIG. 15) including the SID and the position with respect to the irradiation center on the touch panel display 55.

Figure 6:
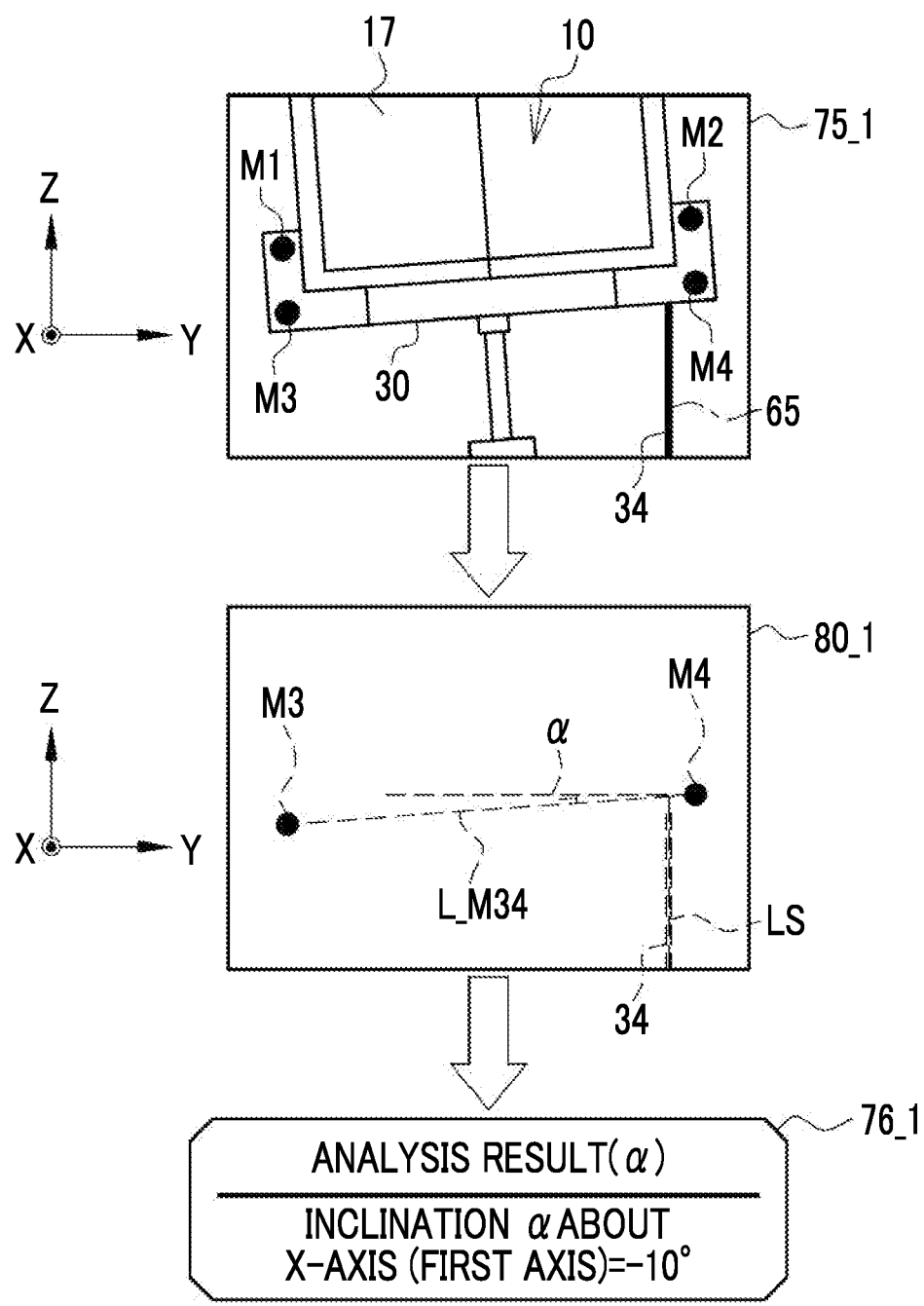
FIG. 6 is a diagram illustrating an aspect in which an inclination of an electronic cassette about an X-axis is detected.

For example, as illustrated as an analysis image 80_1 in FIG. 6, the image analysis unit 70 extracts an image of the marker M3, the marker M4, and the string 34 from a captured image 75_1 captured by the first imaging instruction using a well-known image recognition technique. The image analysis unit 70 calculates an angle formed between a line L_M34 connecting the centers of the markers M3 and the marker M4 and a line LS following the string 34. Then, the image analysis unit 70 detects an angle obtained by subtracting 90° from the calculated angle as an inclination α of the electronic cassette 10 about the X-axis. In a case in which the angle formed between the line L_M34 and the line LS is less than 90° (acute angle) as illustrated in FIG. 6, α is a negative value. On the contrary, in a case in which the angle formed between the line L_M34 and the line LS is greater than 90° (obtuse angle), α is a positive value. In a case in which the angle formed between the line L_M34 and the line LS is 90°, α is 0°. In this case, there is no deviation in the inclination of the electronic cassette 10 about the X-axis. The image analysis unit 70 outputs the detected inclination α of the electronic cassette 10 about the X-axis as an analysis result 76_1 to the displacement amount calculation unit 71 and the like. FIG. 6 illustrates a case in which the angle formed between the line L_M34 and the line LS is 80° and α is 80°−90°=−10°.

Figure 7:
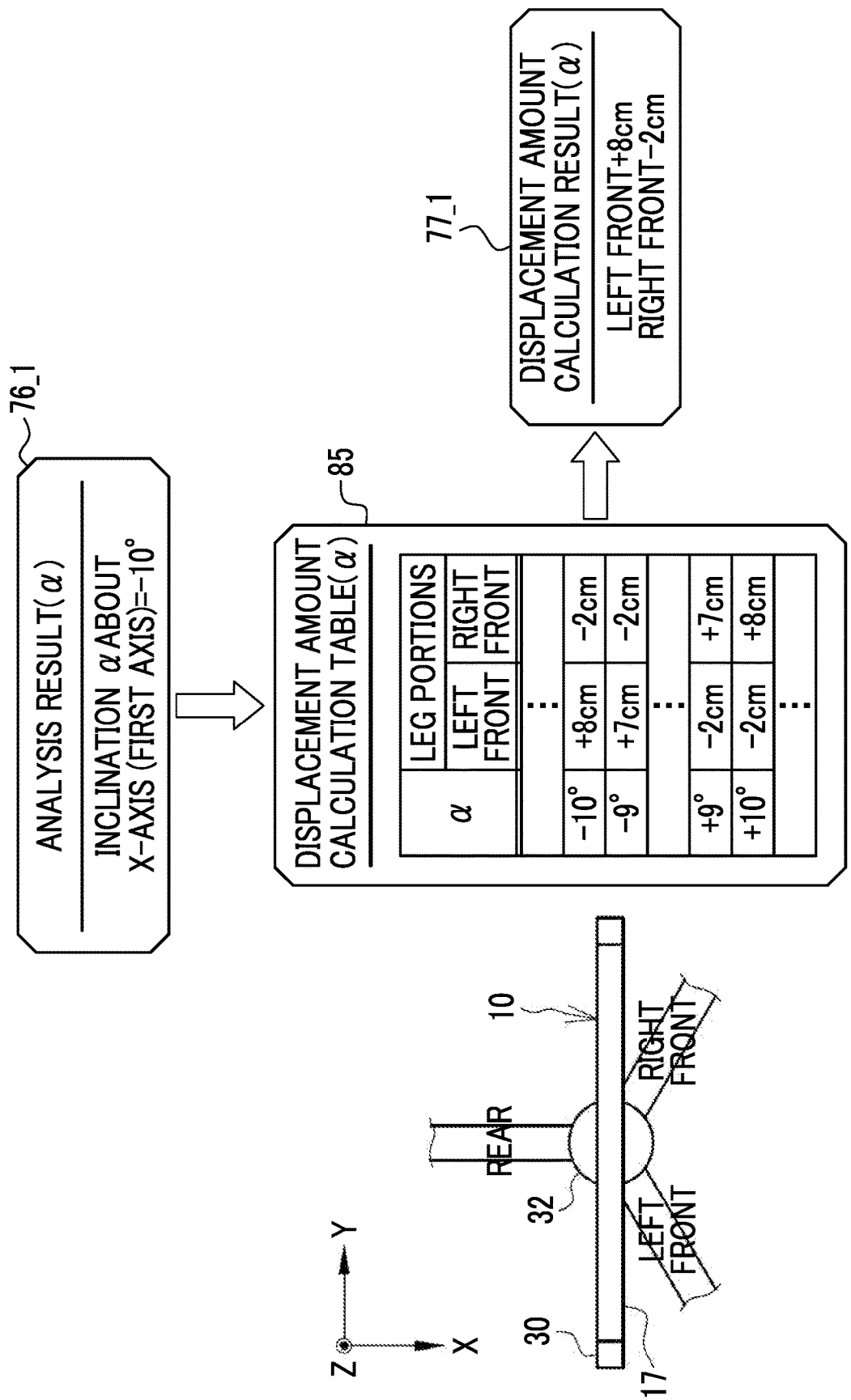
FIG. 7 is a diagram illustrating an aspect in which an amount of displacement reducing the deviation of the inclination of the electronic cassette about the X-axis is calculated.

For example, as illustrated in FIG. 7, the displacement amount calculation unit 71 calculates the amount of displacement for reducing the deviation of the inclination of the electronic cassette 10 about the X-axis with reference to a displacement amount calculation table 85. The displacement amount calculation table 85 is stored in the storage 56. The amount of displacement of the movable portion 39 is registered for each inclination α of the electronic cassette 10 about the X-axis in the displacement amount calculation table 85. The displacement amount calculation unit 71 reads an amount of displacement corresponding to the inclination α of the electronic cassette 10 about the X-axis included in the analysis result 76_1 from the image analysis unit 70 from the displacement amount calculation table 85 and outputs the read amount of displacement as a displacement amount calculation result 77_1 to the display control unit 72.

Here, of two leg portions 33 extending in the directions which are symmetric with respect to the detection surface 17 of the electronic cassette 10, specifically, in the directions having an angle of 30° from the detection surface 17, the leg portion 33 that is located on the left side of the subject H is referred to as a left front leg portion 33, and the leg portion 33 that is located on the right side of the subject H is referred to as a right front leg portion 33. In addition, the leg portion 33 at the position orthogonal to the detection surface 17 of the electronic cassette 10 is referred to as a rear leg portion 33. In this case, even though the movable portion 39 of the rear leg portion 33 is displaced, the inclination of the electronic cassette 10 about the X-axis is not changed. Therefore, the amounts of displacement of the movable portions 39 of the right front and left front leg portions 33 are registered in the displacement amount calculation table 85, but the amount of displacement of the movable portion 39 of the rear leg portion 33 is not registered in the displacement amount calculation table 85. FIG. 7 illustrates a case in which the displacement amount calculation result 77_1 showing that the inclination α of the electronic cassette 10 about the X-axis included in the analysis result 76_1 is −10°, the amount of displacement of the movable portion 39 of the left front leg portion 33 is +8 cm, and the amount of displacement of the movable portion 39 of the right front leg portion 33 is −2 cm is calculated. In addition, in a case in which the movable portion 39 of one of the right front leg portion 33 and the left front leg portion 33 is displaced, the inclination of the electronic cassette 10 about the X-axis is changed. Therefore, only the amount of displacement of the movable portion 39 of one of the right front leg portion 33 and the left front leg portion 33 may be registered in the displacement amount calculation table 85.

Figure 8:
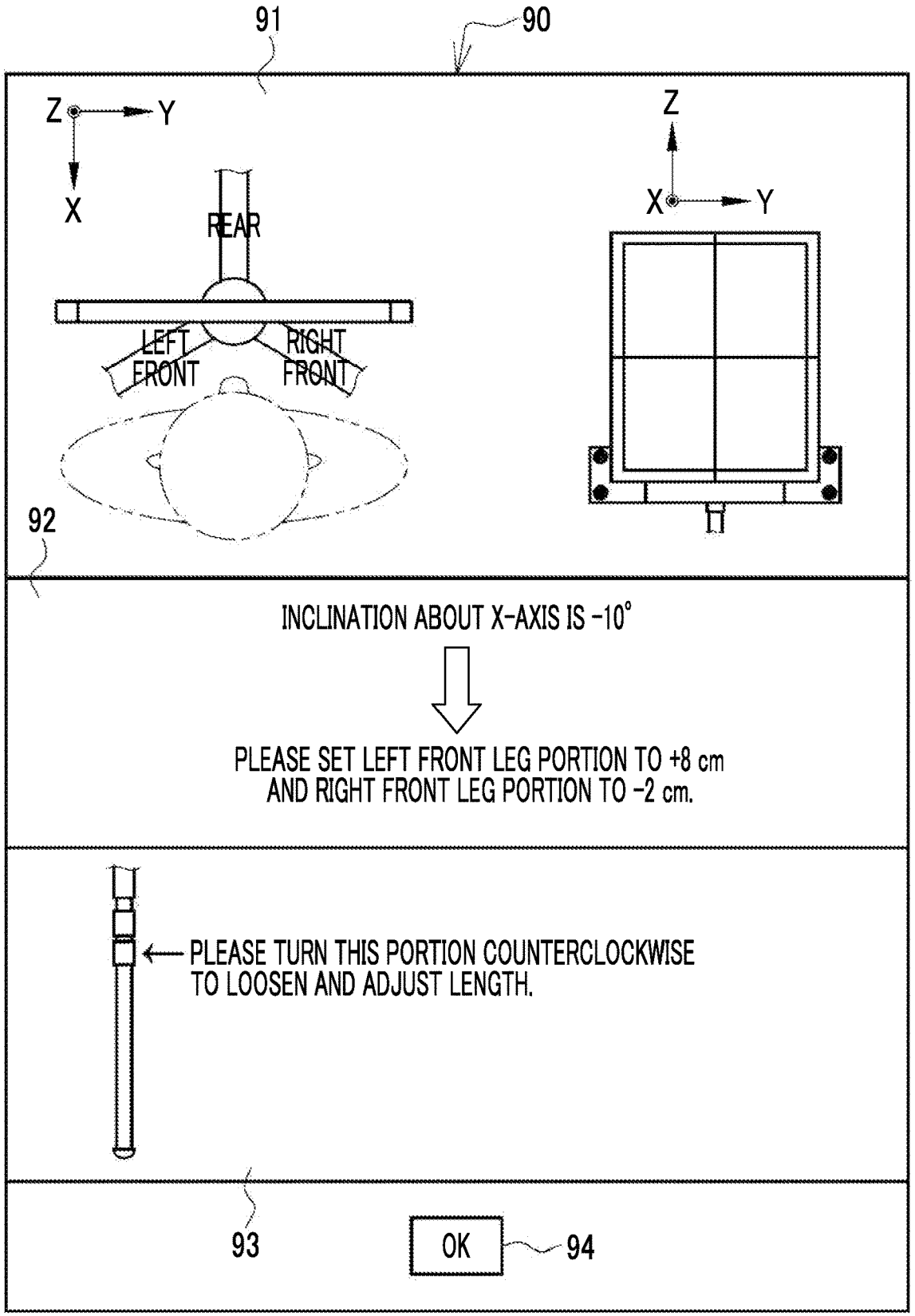
FIG. 8 is a diagram illustrating a first notification screen.

For example, as illustrated in FIG. 8, the first notification screen 90 displayed on the touch panel display 55 after the first imaging instruction includes an illustration display region 91, a result display region 92, and a guide display region 93. An illustration showing the first retainer 14 to which the electronic cassette 10 is attached and the subject H in a plan view from the Z-axis direction and an illustration showing the electronic cassette 10 and the holder 30 in a plan view from the X-axis direction are displayed in the illustration display region 91. In the illustration showing the first retainer 14 to which the electronic cassette 10 is attached and the subject H in a plan view from the Z-axis direction, the words "left front", "right front", and "rear" for distinguishing the leg portions 33A to 33C are displayed.

The analysis result 76_1 and the displacement amount calculation result 77_1 are displayed in the result display region 92. Specifically, the inclination α of the electronic cassette 10 about the X-axis and the amount of displacement of the movable portion 39 for reducing the deviation of the inclination of the electronic cassette 10 about the X-axis are displayed in the result display region 92. A guide indicating how to adjust the length of the movable portion 39 is displayed in the guide display region 93. In addition, in a case in which α is 0°, the displacement amount calculation result 77_1 is not displayed in the result display region 92, and a message indicating that the adjustment of the length of the movable portion 39 is not required is displayed.

Further, there may be a case in which the inclination of the radiation source 11 about the X-axis deviates and the line LS following the string 34 is not captured in parallel to the left and right sides of the analysis image 80_1. In this case, the angle formed between the line LS following the string 34 and the left and right sides of the analysis image 80_1 is calculated as the inclination of the radiation source 11 about the X-axis, and the amount of displacement of the movable portion of the second retainer 16 for reducing the inclination of the radiation source 11 about the X-axis is calculated. Then, the inclination of the radiation source 11 about the X-axis and the amount of displacement of the movable portion of the second retainer 16 for reducing the inclination of the radiation source 11 about the X-axis are displayed on the first notification screen 90 to prompt the operator OP to adjust the length of the movable portion of the second retainer 16.

An OK button 94 is provided in a lower portion of the first notification screen 90. The operator OP displaces the movable portion 39 with reference to the graduations on the basis of the display of the result display region 92 and then selects the OK button 94. In a case in which the OK button 94 is selected, the second imaging instruction is issued. In addition, after the selection of the OK button 94, in a case in which the deviation of the inclination of the electronic cassette 10 about the X-axis has not been sufficiently reduced, the second imaging instruction is not issued, and the operator OP is prompted to adjust the length of the movable portion 39 again. Here, the case in which the deviation of the inclination of the electronic cassette 10 about the X-axis has not been sufficiently reduced is a case in which the inclination α of the electronic cassette 10 about the X-axis has not been 0° or a case in which the inclination α has not fallen within a preset allowable range having 0° as its center (for example, −1°<α<+1°).

Figure 9:
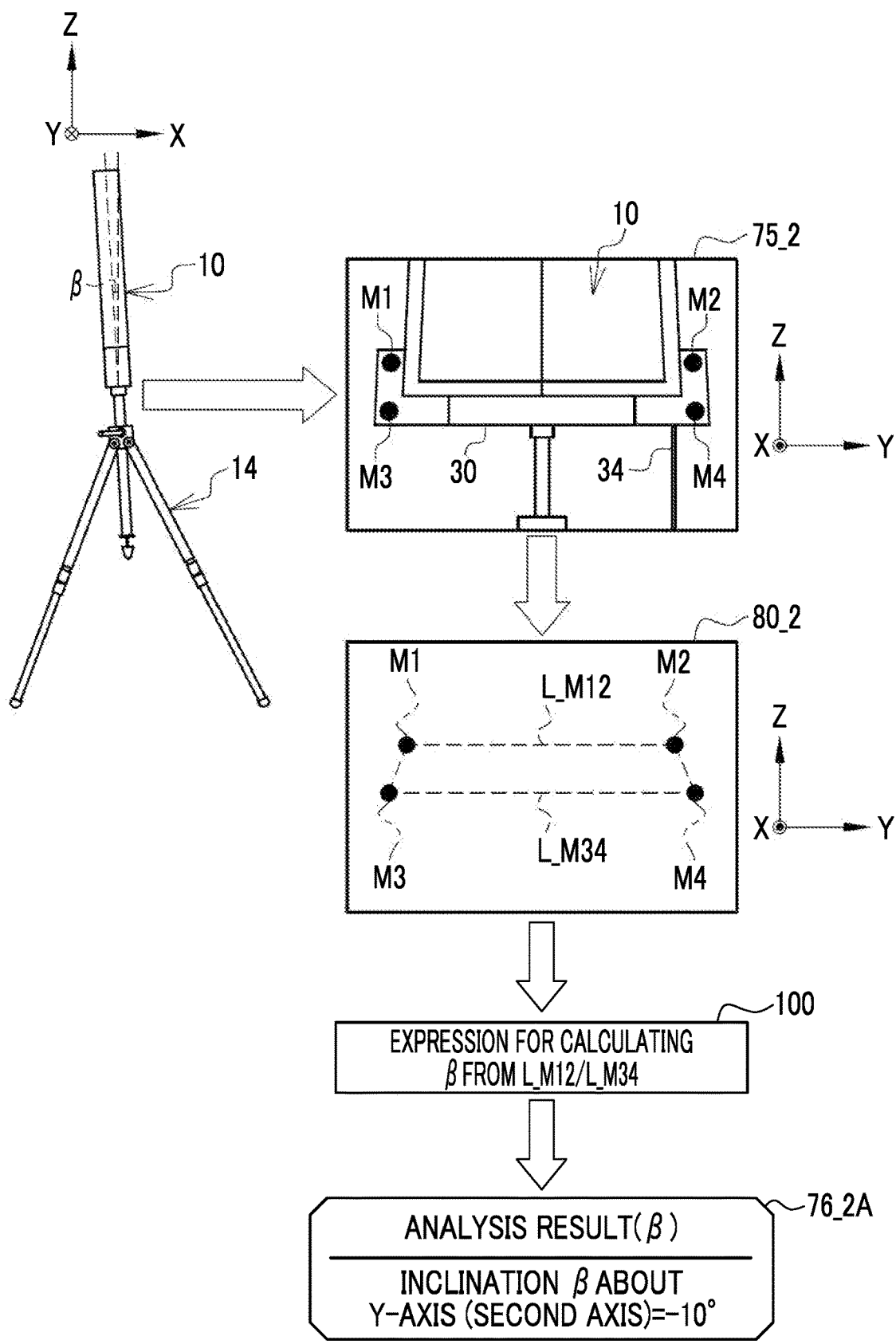
FIG. 9 is a diagram illustrating an aspect in which an inclination of the electronic cassette about a Y-axis is detected.

For example, as illustrated as an analysis image 80_2 in FIG. 9, the image analysis unit 70 extracts the image of the markers M1 to M4 from a captured image 75_2 captured by the second imaging instruction using a well-known image recognition technique. The image analysis unit 70 calculates the length of a line L_M12 connecting the centers of the marker M1 and the marker M2 and the length of a line L_M34 connecting the centers of the marker M3 and the marker M4. Then, the image analysis unit 70 calculates an inclination β of the electronic cassette 10 about the Y-axis using an expression 100 for calculating the inclination β of the electronic cassette 10 about the Y-axis from a ratio L_M12/L_M34 of the length of the line L_M12 to the length of the line L_M34. The expression 100 is an equation that has the ratio L_M12/L_M34 as a variable and β as a solution and is stored in the storage 56. In a case in which the electronic cassette 10 is inclined to the rear as illustrated in FIG. 9, the length of the line L_M12 is smaller than the length of the line L_M34, and the ratio L_M12/L_M34 is smaller than 1. In this case, β has a negative value. On the contrary, in a case in which the electronic cassette 10 is inclined to the front, the length of the line L_M12 is larger than the length of the line L_M34, and the ratio L_M12/L_M34 is larger than 1. In this case, β has a positive value. In a case in which the detection surface 17 of the electronic cassette 10 is parallel to the Z-axis, the length of the line L_M12 is equal to the length of the line L_M34, and the ratio L_M12/L_M34 is 1. In this case, β is 0°, and there is no deviation in the inclination of the electronic cassette 10 about the Y-axis. The image analysis unit 70 outputs the calculated β as an analysis result 76_2A to the displacement amount calculation unit 71 and the like.

Figure 10:
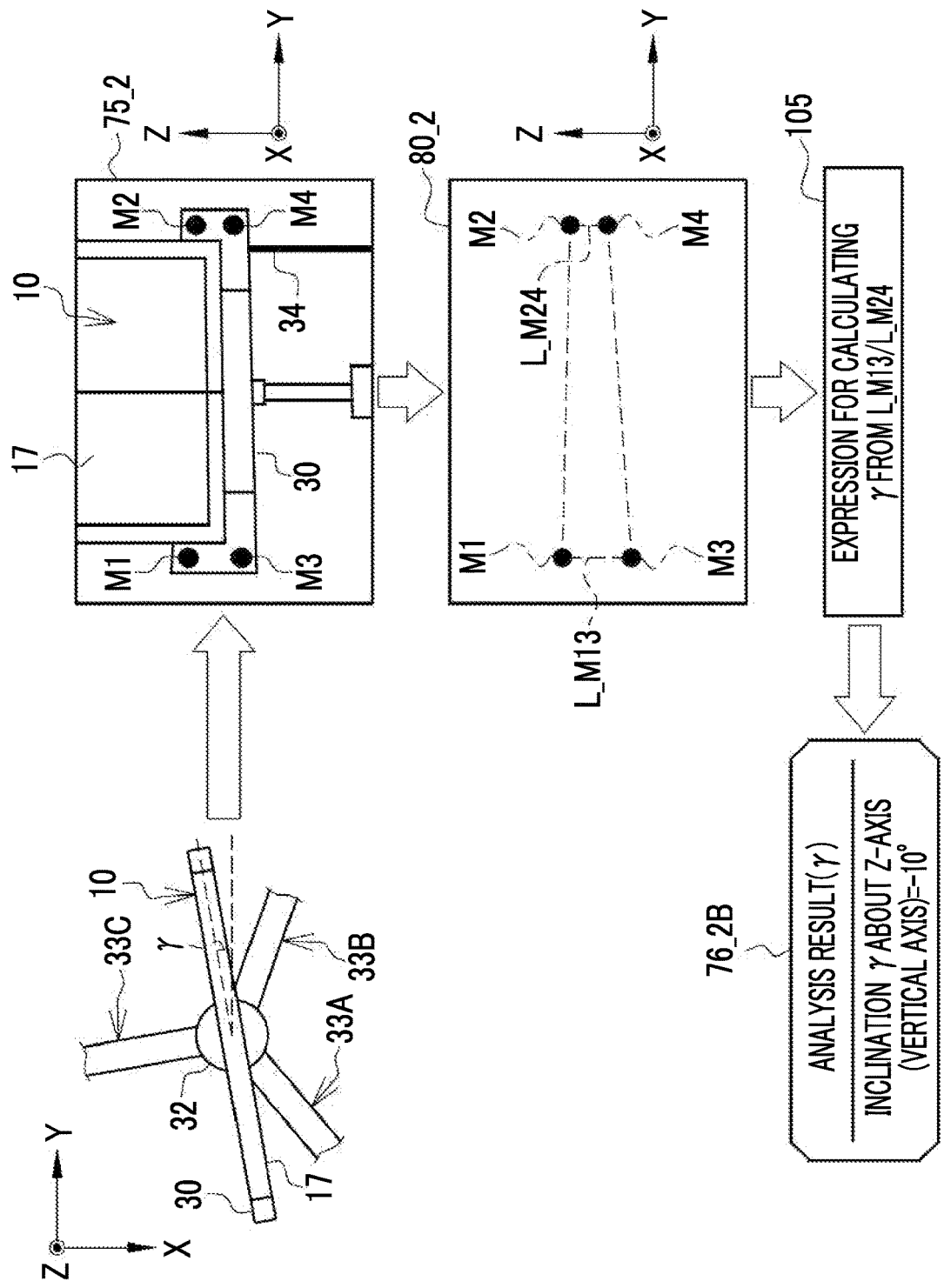
FIG. 10 is a diagram illustrating an aspect in which an inclination of the electronic cassette about a Z-axis is detected.

Further, for example, as illustrated in FIG. 10, the image analysis unit 70 calculates the length of a line L_M13 connecting the centers of the markers M1 and the marker M3 and the length of a line L_M24 connecting the centers of the marker M2 and the marker M4 in the analysis image 80_2 of the captured image 75_2 captured by the second imaging instruction. Then, the image analysis unit 70 calculates an inclination γ of the electronic cassette 10 about the Z-axis from a ratio L_M13/L_M24 of the length of the line L_M13 to the length of the line L_M24 using an expression 105 for calculating the inclination γ of the electronic cassette 10 about the Z-axis. The expression 105 is an equation that has the ratio L_M13/L_M24 as a variable and γ as a solution and is stored in the storage 56. In a case in which the electronic cassette 10 is inclined to the left as illustrated in FIG. 10, the length of the line L_M13 is larger than the length of the line L_M24, and the ratio L_M13/L_M24 is larger than 1. In this case, γ has a negative value. On the contrary, in a case in which the electronic cassette 10 is inclined to the right, the length of the line L_M13 is smaller than the length of the line L_M24, and the ratio L_M13/L_M24 is smaller than 1. In this case, γ has a positive value. In a case in which the detection surface 17 of the electronic cassette 10 is parallel to the Y-axis, the length of the line L_M13 is equal to the length of the line L_M24, and the ratio L_M13/L_M24 is 1. In this case, γ is 0°, and there is no deviation in the inclination of the electronic cassette 10 about the Z-axis. The image analysis unit 70 outputs the calculated γ as an analysis result 76_2B to the displacement amount calculation unit 71 and the like. In addition, for convenience, the process illustrated in FIG. 9 for calculating the inclination β of the electronic cassette 10 about the Y-axis and the process illustrated in FIG. 10 for calculating the inclination γ of the electronic cassette 10 about the Z-axis have been described separately. However, the image analysis unit 70 performs the processes illustrated in FIGS. 9 and 10 in parallel.

Figure 11:
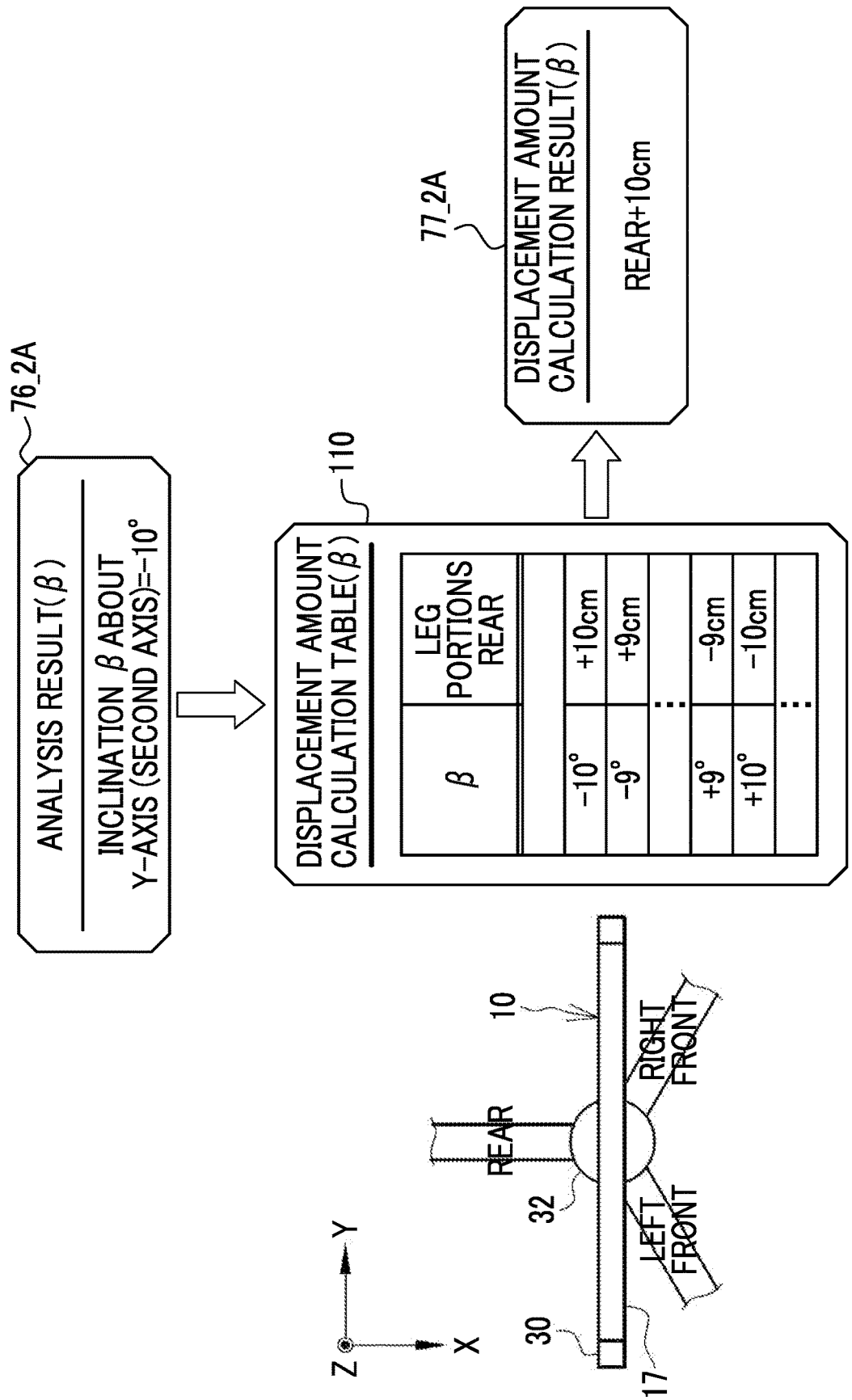
FIG. 11 is a diagram illustrating an aspect in which an amount of displacement for reducing the deviation of the inclination of the electronic cassette about the Y-axis is calculated.

For example, as illustrated in FIG. 11, the displacement amount calculation unit 71 calculates the amount of displacement for reducing the deviation of the inclination of the electronic cassette 10 about the Y-axis with reference to a displacement amount calculation table 110. The displacement amount calculation table 110 is stored in the storage 56. The amount of displacement of the movable portion 39 is registered for each inclination β of the electronic cassette 10 about the Y-axis in the displacement amount calculation table 110. The displacement amount calculation unit 71 reads an amount of displacement corresponding to the inclination β of the electronic cassette 10 about the Y-axis included in the analysis result 76_2A from the image analysis unit 70 from the displacement amount calculation table 110 and outputs the read amount of displacement as a displacement amount calculation result 77_2A to the display control unit 72.

In a case in which the inclination of the electronic cassette 10 about the Y-axis is changed, it is better to displace only the movable portion 39 of the rear leg portion 33 than to displace both the movable portions 39 of the right front and left front leg portions 33 by the same amount, in order to reduce the time required for adjustment. Therefore, the amounts of displacement of the movable portions 39 of the right front and left front leg portions 33 are not registered in the displacement amount calculation table 110, and only the amount of displacement of the movable portion 39 of the rear leg portion 33 is registered in the displacement amount calculation table 110. FIG. 11 illustrates a case in which the displacement amount calculation result 77_2A showing that the inclination β of the electronic cassette 10 about the Y-axis included in the analysis result 76_2A is −10° and the amount of displacement of the movable portion 39 of the rear leg portion 33 is +10 cm is calculated.

The deviation of the inclination of the electronic cassette 10 about the Z-axis is not reduced even in a case in which the movable portion 39 is displaced. Therefore, the deviation of the inclination of the electronic cassette 10 about the Z-axis is reduced by rotating the electronic cassette 10 about the Z-axis for each first retainer 14.

Figure 12:
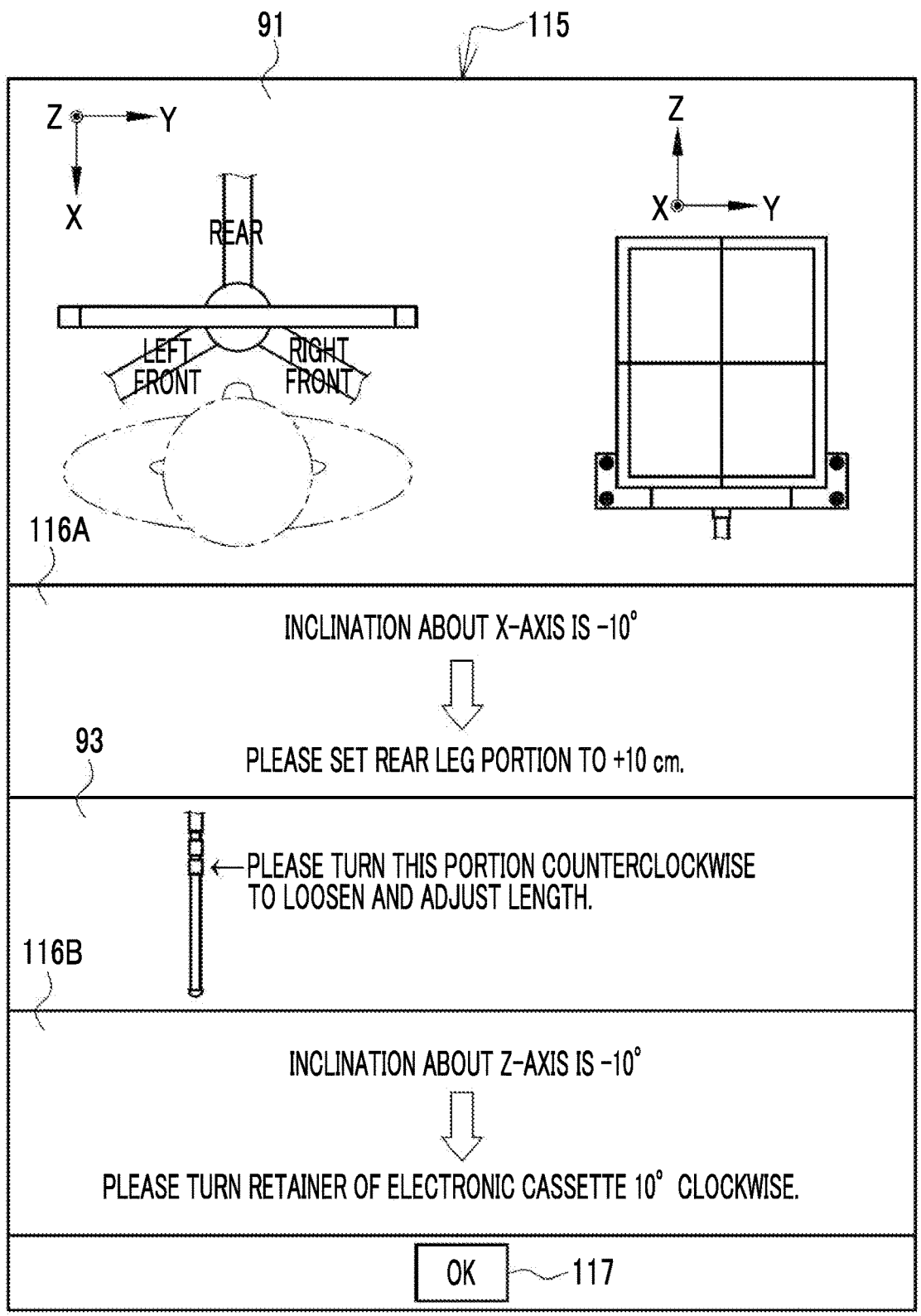
FIG. 12 is a diagram illustrating a second notification screen.

For example, as illustrated in FIG. 12, the second notification screen 115 displayed on the touch panel display 55 after the second imaging instruction includes the same illustration display region 91 and guide display region 93 as the first notification screen 90 and result display regions 116A and 116B. The analysis result 76_2A and the displacement amount calculation result 77_2A are displayed in the result display region 116A. Specifically, the inclination β of the electronic cassette 10 about the Y-axis and the amount of displacement of the movable portion 39 for reducing the deviation of the inclination of the electronic cassette 10 about the Y-axis are displayed in the result display region 116A. Further, in a case in which β is 0°, the displacement amount calculation result 77_2A is not displayed in the result display region 116A, and a message indicating that the adjustment of the length of the movable portion 39 is not required is displayed.

The analysis result 76_2B, specifically, the inclination γ of the electronic cassette 10 about the Z-axis is displayed in the result display region 116B. In addition, the rotation direction and the amount of rotation of the first retainer 14 for reducing the deviation of the inclination of the electronic cassette 10 about the Z-axis which is derived from the analysis result 76_2B are displayed in the result display region 116B. Further, in a case in which γ is 0°, the rotation direction and the amount of rotation of the first retainer 14 are not displayed, and a message indicating that the adjustment of the orientation of the first retainer 14 is not necessary is displayed.

An OK button 117 is provided in a lower portion of the second notification screen 115. The operator OP displaces the movable portion 39 or the first retainer 14 with reference to the graduations on the basis of the display of the result display regions 116A and 116B and then selects the OK button 117. In a case in which the OK button 117 is selected, the third imaging instruction is issued. In addition, after the selection of the OK button 117, in a case in which the deviation of the inclination of the electronic cassette 10 about the Y-axis and/or the Z-axis has not been sufficiently reduced, the third imaging instruction is not issued, and the operator OP is prompted to adjust the length of the movable portion 39 again. Here, the case in which the deviation of the inclination of the electronic cassette 10 about the Y-axis and/or the Z-axis has not been sufficiently reduced is a case in which the inclination $\beta$ and/or the inclination $\gamma$ of the electronic cassette 10 about the Y-axis and/or the Z-axis has not been 0° or a case in which the inclination $\beta$ and/or the inclination $\gamma$ has not fallen within a preset allowable range having 0° as its center (for example, $-1°<\beta<+1°$, $-1°<\gamma<+1°$).

Figure 13:
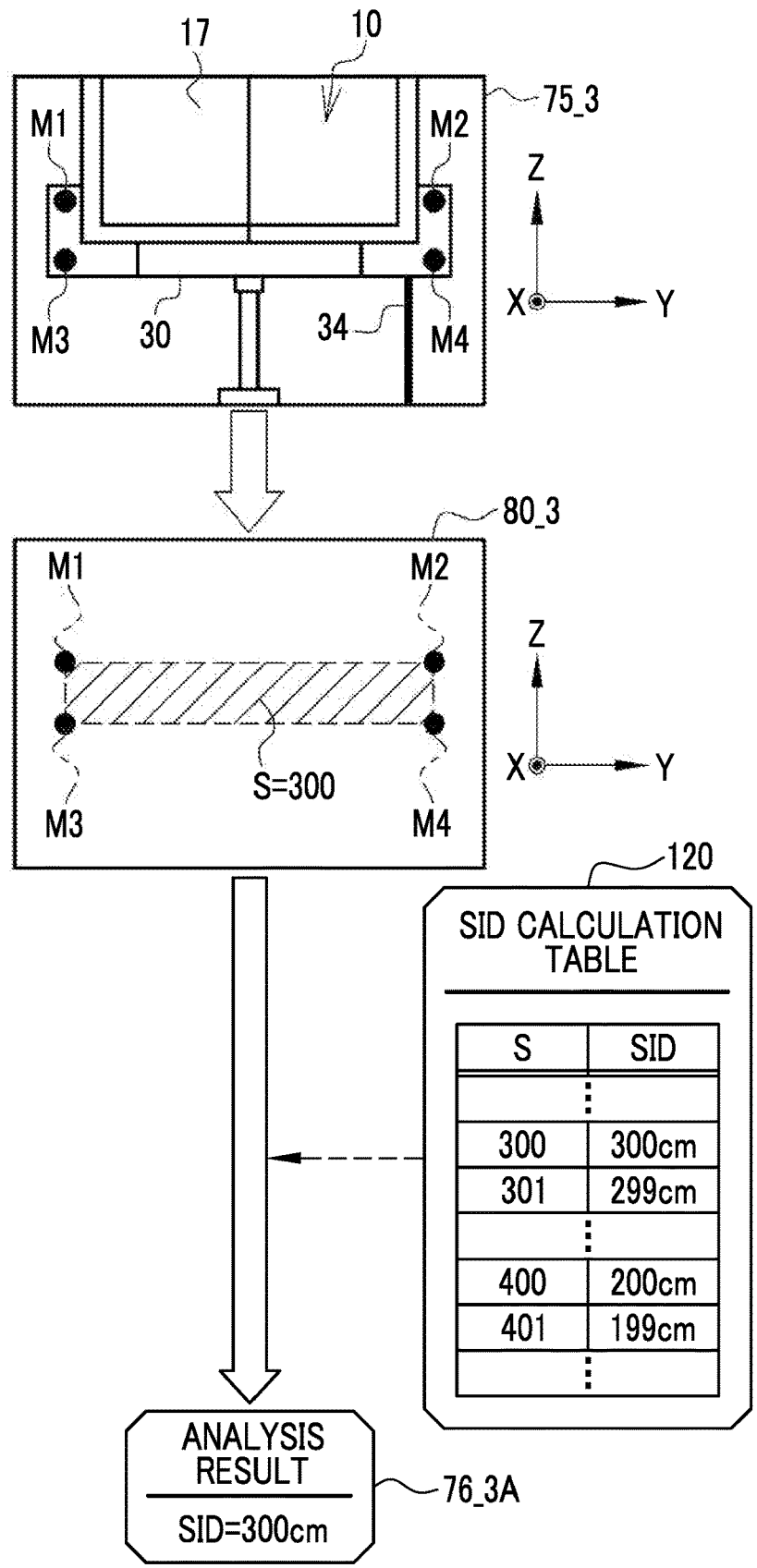
FIG. 13 is a diagram illustrating an aspect in which an SID is detected.

For example, as illustrated as an analysis image 80_3 in FIG. 13, the image analysis unit 70 extracts an image of the markers M1 to M4 from a captured image 75_3 captured by the third imaging instruction using a well-known image recognition technique. The image analysis unit 70 calculates an area S of a rectangle surrounded by lines connecting the centers of the markers M1 to M4. In addition, the image recognition technique by which the image analysis unit 70 extracts the image of the markers M1 to M4 and the string 34 from the analysis image 80 also includes a technique such as semantic segmentation by a machine learning model using a convolutional neural network.

The image analysis unit 70 calculates the SID from the area S with reference to an SID calculation table 120. The SID is registered for each area S in the SID calculation table 120. The SID calculation table 120 is stored in the storage 56. The SID in a case in which the area S is small is relatively long. The SID in a case in which the area S is large is relatively short. The image analysis unit 70 outputs the calculated SID as an analysis result 76_3A to the display control unit 72. FIG. 13 illustrates a case in which the area S is 300 and 300 cm is calculated as the SID.

Figure 14:
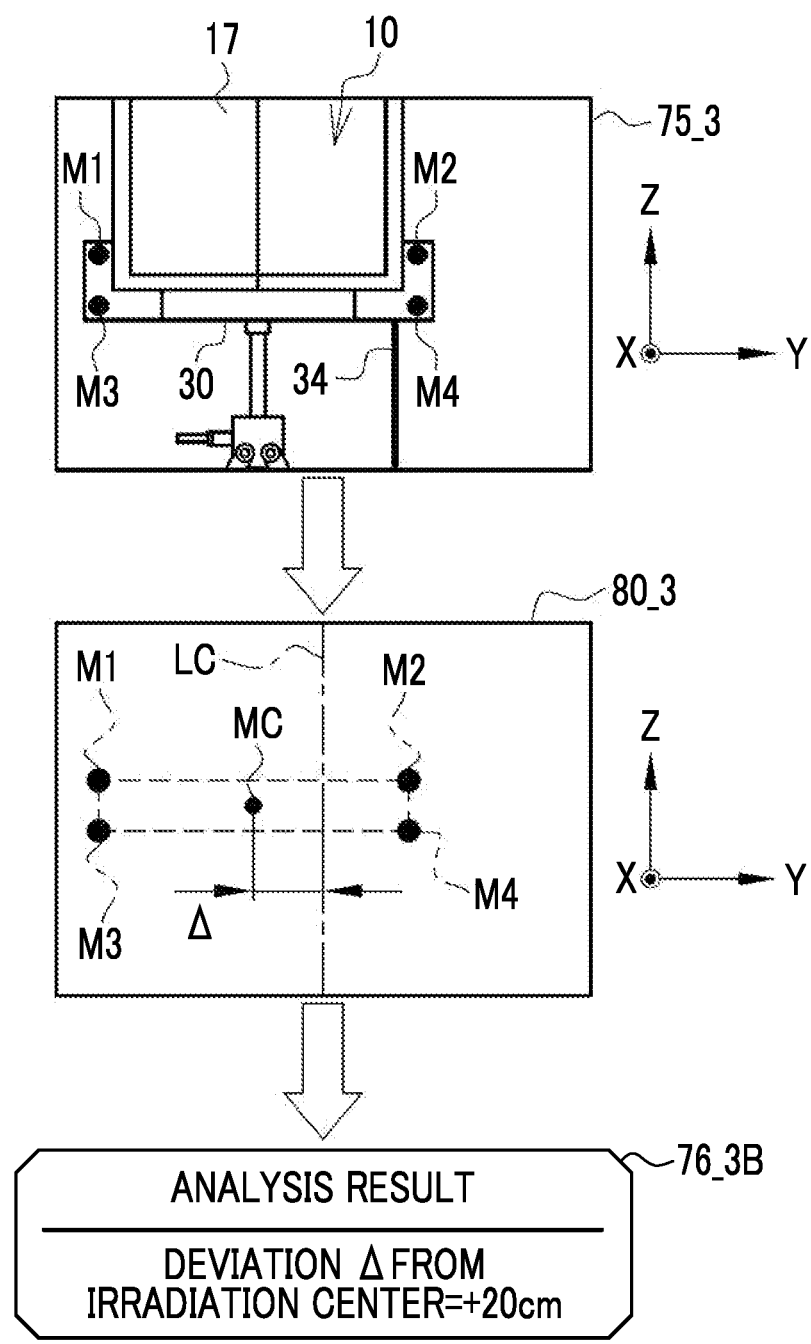
FIG. 14 is a diagram illustrating an aspect in which the deviation of the electronic cassette from an irradiation center in a Y-axis direction is detected.

In addition, for example, as illustrated in FIG. 14, the image analysis unit 70 extracts the center of gravity (here, the center of the rectangle) MC surrounded by the lines connecting the centers of the markers M1 to M4 in the analysis image 80_3 of the captured image 75_3 captured by the third imaging instruction. The image analysis unit 70 calculates an interval $\Delta$ between the extracted center of gravity MC and the line LC, which passes through the center of the captured image 75 and is parallel to the Z-axis, in the Y-axis direction. As described above, the line LC is matched with the line that is parallel to the Z-axis passing through the irradiation center of the radiation R. Therefore, $\Delta$ indicates the deviation of the electronic cassette 10 from the irradiation center in the Y-axis direction (hereinafter, simply referred to as deviation from the irradiation center). That is, $\Delta$ is nothing less than the position with respect to the irradiation center. The image analysis unit 70 outputs the calculated deviation $\Delta$ from the irradiation center as an analysis result 76_3B to the display control unit 72. FIG. 14 illustrates a case in which +20 cm is calculated as the deviation $\Delta$ from the irradiation center. In addition, for convenience, the process illustrated in FIG. 13 for calculating the SID and the process illustrated in FIG. 14 for calculating the deviation $\Delta$ from the irradiation center have been described separately. However, the image analysis unit 70 performs these processes in FIG. 13 and FIG. 14 in parallel.

Figure 15:
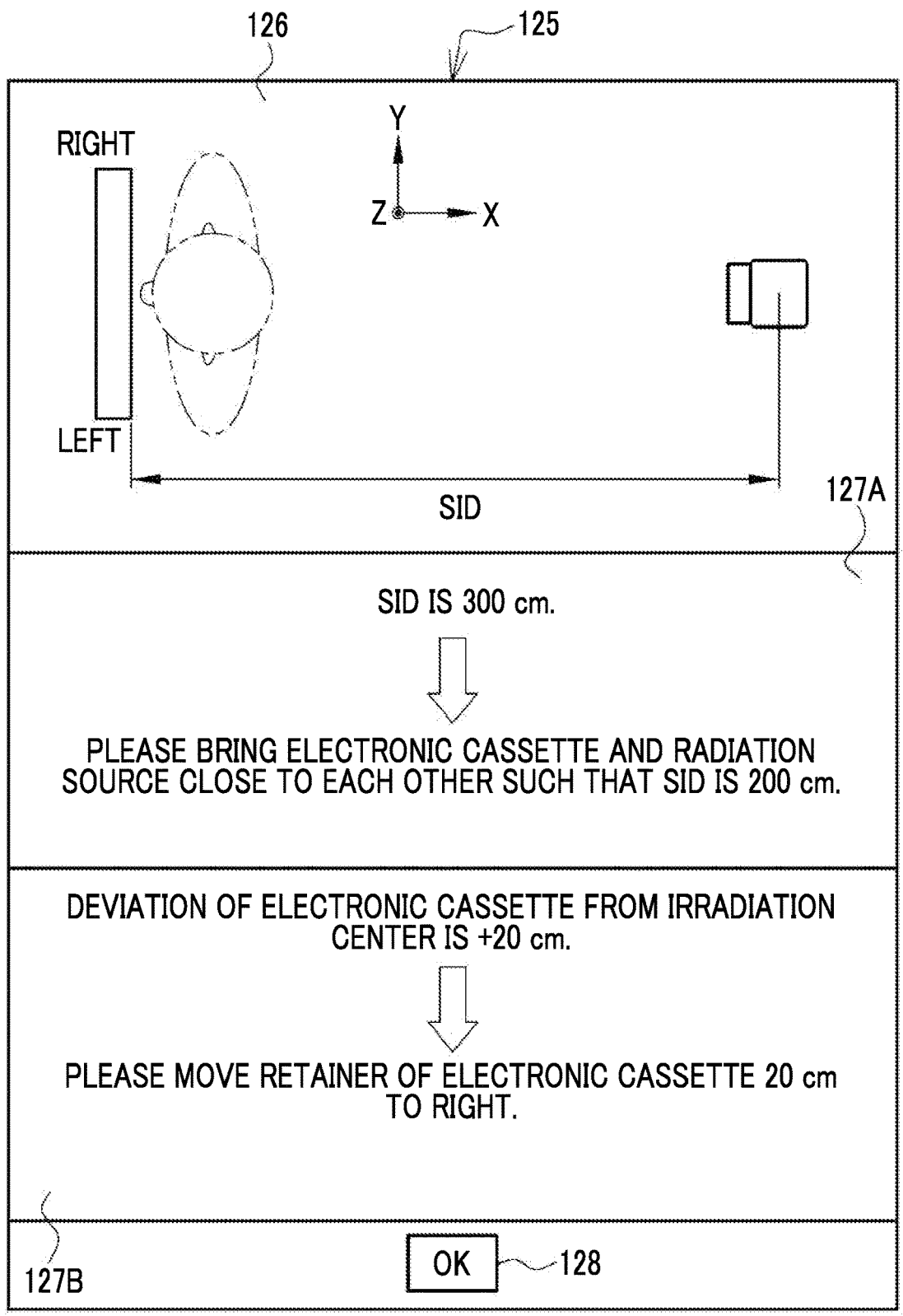
FIG. 15 is a diagram illustrating a third notification screen.

For example, as illustrated in FIG. 15, the third notification screen 125 displayed on the touch panel display 55 after the third imaging instruction includes an illustration display region 126 and result display regions 127A and 127B. An illustration of the electronic cassette 10, the radiation source 11, and the subject H and the SID are displayed in the illustration display region 126. The words "right" and "left" are displayed in the vicinity of the illustration of the electronic cassette 10.

The analysis result 76_3A, specifically, the SID is displayed in the result display region 127A. In addition, the amounts of movement of the electronic cassette 10 and the radiation source 11 in the X-axis direction for making the SID, which is derived from the analysis result 76_3A, have a value associated with the imaging menu is displayed in the result display region 127A. In a case in which the SID has the value associated with the imaging menu, the amounts of movement of the electronic cassette 10 and the radiation source 11 in the X-axis direction are not displayed, and a message indicating that the movement of the electronic cassette 10 and the radiation source 11 in the X-axis direction is not required is displayed.

The analysis result 76_3B, specifically, the deviation $\Delta$ from the irradiation center is displayed in the result display region 127B. In addition, the movement direction and the amount of movement of the first retainer 14 for reducing the deviation $\Delta$ from the irradiation center, which is derived from the analysis result 76_3B, is displayed in the result display region 127B. Here, the amount of movement of the first retainer 14 for reducing the deviation $\Delta$ from the irradiation center is, for example, the amount of movement for eliminating the deviation $\Delta$. The amount of movement for eliminating the deviation $\Delta$ may be the amount of movement for completely eliminating the deviation $\Delta$ and may include an error (for example, an error of about 1% to 10%) that is generally allowed in the technical field to which the technology of the present disclosure belongs and is not contrary to the gist of the technology of the present disclosure. Alternatively, the amount of movement of the first retainer 14 for reducing the deviation $\Delta$ from the irradiation center may be an amount of movement for making the deviation $\Delta$ less than a preset threshold value. In addition, in a case in which there is no deviation $\Delta$ from the irradiation center, the movement direction and the amount of movement of the first retainer 14 are not displayed, and a message indicating that the movement of the first retainer 14 is not required is displayed.

An OK button 128 is provided in a lower portion of the third notification screen 125. The operator OP moves the electronic cassette 10 and the radiation source 11 along the X-axis or moves the first retainer 14 along the Y-axis on the basis of the display of the result display regions 127A and 127B and then selects the OK button 128. In a case in which the OK button 128 is selected, the display is switched to a screen for inputting the instruction to start the emission of the radiation R to the radiation source control device 12. In addition, after the selection of the OK button 128, in a case in which the SID has not been the value associated with the imaging menu and/or in a case in which the deviation $\Delta$ from the irradiation center has not been sufficiently reduced, the display is not changed to the screen for inputting the instruction to start the emission of the radiation R to the radiation source control device 12, and the operator OP is prompted to adjust the positions of the electronic cassette 10 and the radiation source 11 again. Here, the case in which the SID has not been the value associated with the imaging menu is a case in which the SID has not been matched with the value associated with the imaging menu or a case in which the SID has not fallen within a preset allowable range having the value associated with the imaging menu as its center (for example, −5 cm<the value associated with the imaging menu<+5 cm). The case in which the deviation Δ from the irradiation center has not been sufficiently reduced is a case in which the deviation Δ from the irradiation center has not been 0 cm or a case in which the deviation Δ has not fallen within a preset allowable range having 0 cm as its center (for example, −1 cm<Δ<+1 cm).

Figure 16:
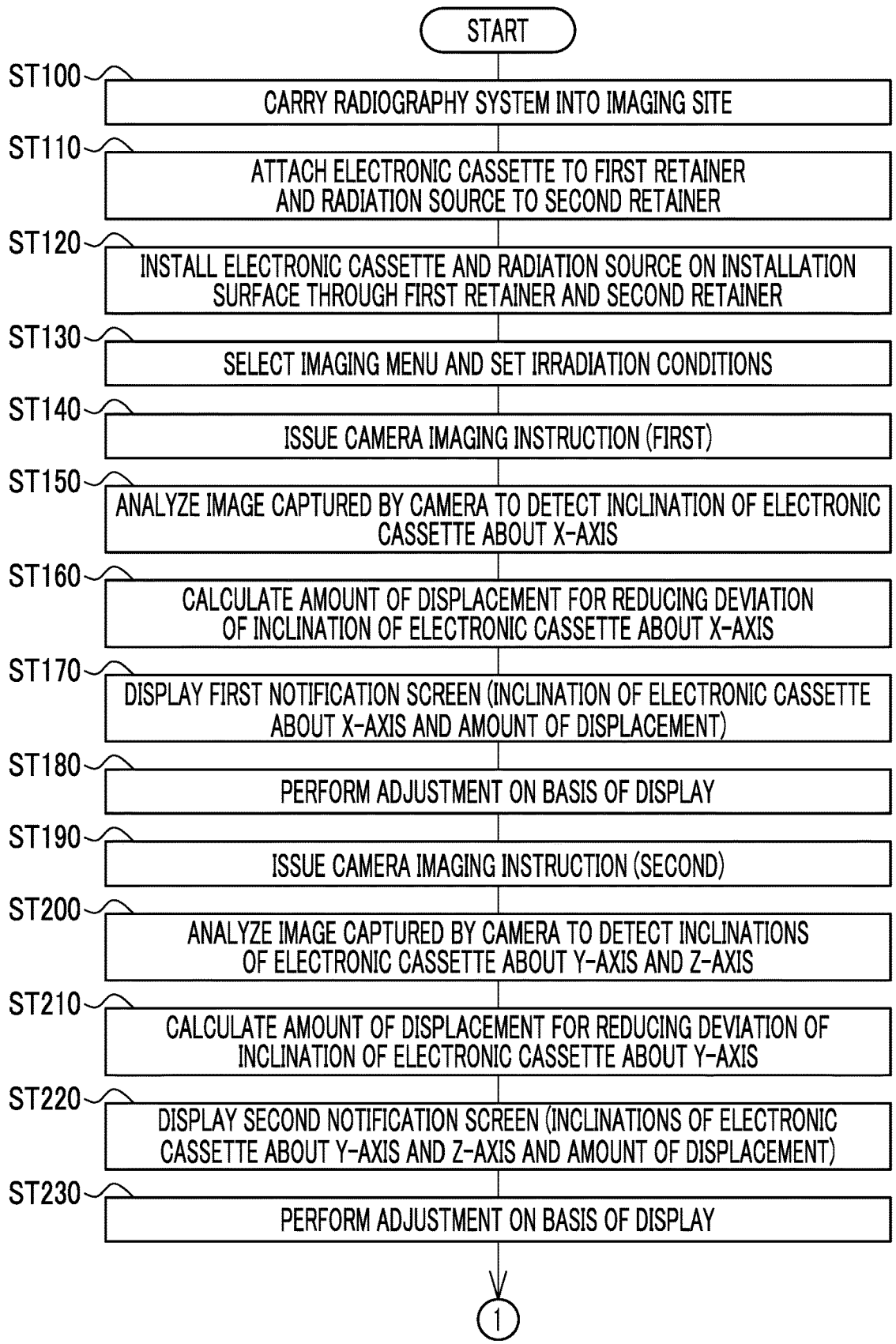
FIG. 16 is a flowchart illustrating a procedure of radiography by the radiography system.

Next, the operation of the above-mentioned configuration will be described with reference to, for example, flowcharts illustrated in FIGS. 16 and 17. First, as illustrated in FIG. 16, the operator OP carries the radiography system 2 (the electronic cassette 10, the radiation source 11, the radiation source control device 12, the console 13, the first retainer 14, and the second retainer 16) into an imaging site (Step ST100). The operator OP attaches the electronic cassette 10 to the first retainer 14 and the radiation source 11 to the second retainer 16 (Step ST110). Then, the electronic cassette 10 and the radiation source 11 are installed (temporarily placed) on the installation surface 15 at the imaging site through the first retainer 14 and the second retainer 16 (Step ST120). In this case, the operator OP disposes the electronic cassette 10 such that the detection surface 17 is along the Z-axis as much as possible. In addition, the operator OP disposes the detection surface 17 of the electronic cassette 10 and the radiation source 11 to face each other such that at least the markers M3 and M4 and the string 34 come within the angle of view of the camera 20.

The operator OP operates the console 13 to select an imaging menu and to set the irradiation conditions of the radiation R (Step ST130). Then, the operator OP operates the console 13 to issue the first imaging instruction to the camera 20 (Step ST140). The captured image 75_1 is captured by the camera 20 in response to the first imaging instruction.

As illustrated in FIG. 6, the image analysis unit 70 analyzes the captured image 75_1 to detect the inclination α of the electronic cassette 10 about the X-axis (Step ST150). The analysis result 76_1 including the inclination α of the electronic cassette 10 about the X-axis is output from the image analysis unit 70 to the displacement amount calculation unit 71 and the display control unit 72.

As illustrated in FIG. 7, the displacement amount calculation unit 71 calculates the amount of displacement of the movable portion 39 for reducing the deviation of the inclination of the electronic cassette 10 about the X-axis with reference to the displacement amount calculation table 85 (Step ST160). The displacement amount calculation result 77_1 is output from the displacement amount calculation unit 71 to the display control unit 72.

As illustrated in FIG. 8, the first notification screen 90 is displayed on the touch panel display 55 of the console 13 under the control of the display control unit 72 (Step ST170). The first notification screen 90 has the result display region 92 in which the inclination α of the electronic cassette 10 about the X-axis and the amount of displacement of the movable portion 39 for reducing the deviation of the inclination of the electronic cassette 10 about the X-axis are displayed. The operator OP adjusts the length of the movable portion 39 on the basis of the display of the result display region 92 (Step ST180). In a case in which the inclination α of the electronic cassette 10 about the X-axis is 0°, Step ST180 is omitted.

The operator OP selects the OK button 94 on the first notification screen 90 to issue the second imaging instruction to the camera 20 (Step ST190). The captured image 75_2 is captured by the camera 20 in response to the second imaging instruction.

As illustrated in FIGS. 9 and 10, the image analysis unit 70 analyzes the captured image 75_2 to detect the inclinations β and γ of the electronic cassette 10 about the Y-axis and the Z-axis (Step ST200). The analysis result 76_2A including the inclination β of the electronic cassette 10 about the Y-axis is output from the image analysis unit 70 to the displacement amount calculation unit 71 and the display control unit 72. Further, the analysis result 76_2B including the inclination γ of the electronic cassette 10 about the Z-axis is output from the image analysis unit 70 to the display control unit 72.

As illustrated in FIG. 11, the displacement amount calculation unit 71 calculates the amount of displacement of the movable portion 39 for reducing the deviation of the inclination of the electronic cassette 10 about the Y-axis with reference to the displacement amount calculation table 110 (Step ST210). The displacement amount calculation result 77_2A is output from the displacement amount calculation unit 71 to the display control unit 72.

As illustrated in FIG. 12, the second notification screen 115 is displayed on the touch panel display 55 of the console 13 under the control of the display control unit 72 (Step ST220). The second notification screen 115 has the result display region 116A in which the inclination β of the electronic cassette 10 about the Y-axis and the amount of displacement of the movable portion 39 for reducing the deviation of the inclination of the electronic cassette 10 about the Y-axis are displayed. In addition, the second notification screen 115 has the result display region 116B in which the inclination γ of the electronic cassette 10 about the Z-axis and the rotation direction and the amount of rotation of the first retainer 14 for reducing the deviation of the inclination of the electronic cassette 10 about the Z-axis are displayed. The operator OP adjusts, for example, the length of the movable portion 39 on the basis of the display of the result display regions 116A and 116B (Step ST230). In a case in which the inclination β of the electronic cassette 10 about the Y-axis is 0° and the inclination γ of the electronic cassette 10 about the Z-axis is 0°, Step ST230 is omitted.

Figure 17:
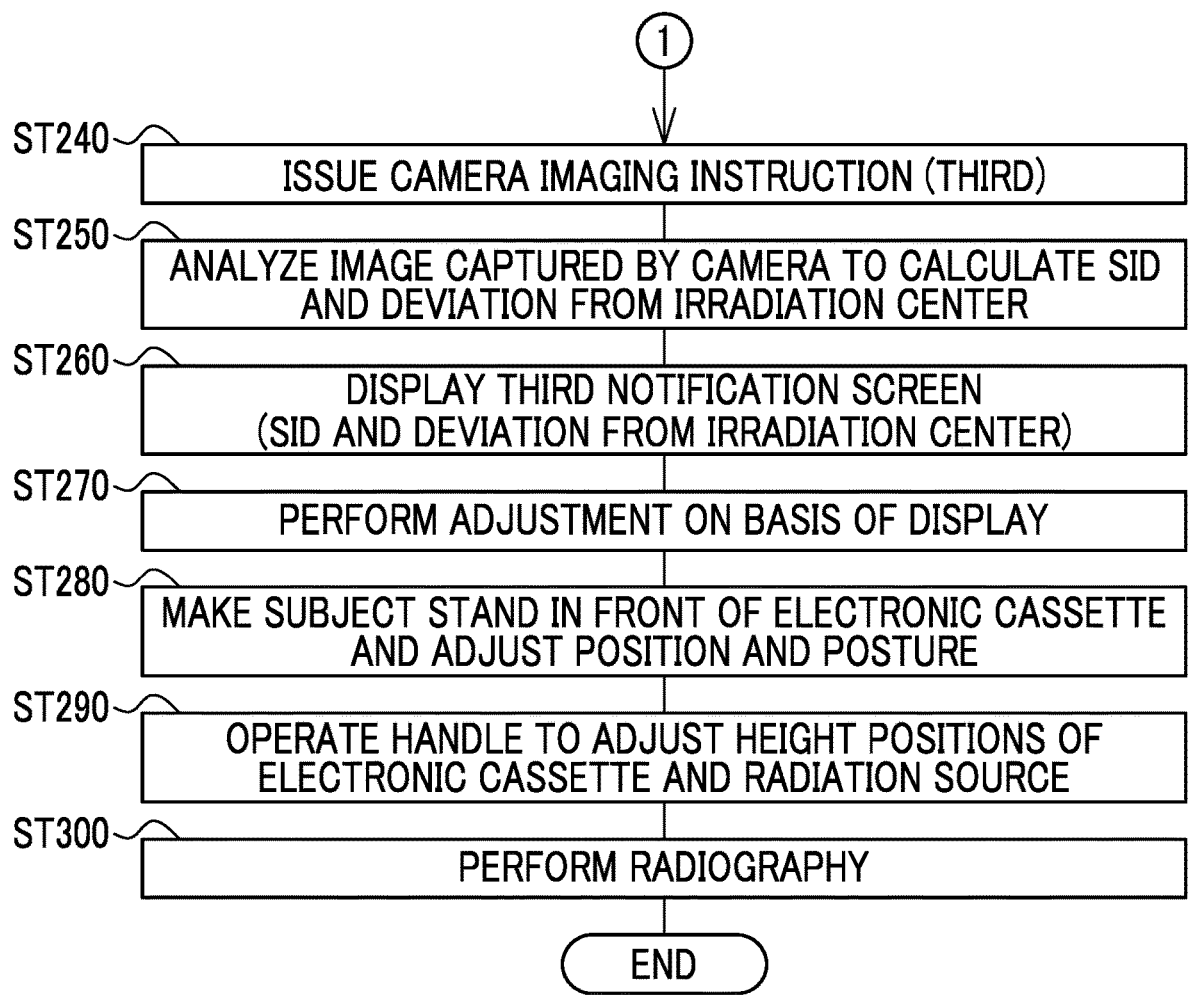
FIG. 17 is a flowchart illustrating the procedure of the radiography by the radiography system.

As illustrated in FIG. 17, the operator OP selects the OK button 117 on the second notification screen 115 to issue the third imaging instruction to the camera 20 (Step ST240). The captured image 75_3 is captured by the camera 20 in response to the third imaging instruction.

As illustrated in FIG. 13, the image analysis unit 70 analyzes the captured image 75_3 to calculate the area S of the rectangle surrounded by the lines connecting the centers of the markers M1 to M4. Then, the SID is calculated from the area S with reference to the SID calculation table 120 (Step ST250). In addition, as illustrated in FIG. 14, the deviation Δ from the irradiation center is calculated (Step ST250). The analysis result 76_3A including the SID and the analysis result 76_3B including the deviation Δ from the irradiation center are output from the image analysis unit 70 to the display control unit 72.

As illustrated in FIG. 15, the third notification screen 125 is displayed on the touch panel display 55 of the console 13 under the control of the display control unit 72 (Step ST260). The third notification screen 125 has the result display region 127A in which the SID and the amounts of movement of the electronic cassette 10 and the radiation source 11 in the X-axis direction for making the SID have the value associated with the imaging menu are displayed. In addition, the third notification screen 125 has the result display region 127B in which the deviation Δ from the irradiation center and the movement direction and the amount of movement of the first retainer 14 for reducing the deviation Δ from the irradiation center are displayed. The operator OP adjusts the positions of the electronic cassette 10 and the radiation source 11 (the positions of the first retainer 14 and the second retainer 16) on the basis of the display of the result display regions 127A and 127B (Step ST270). In a case in which the SID is the value associated with the imaging menu and there is no deviation Δ from the irradiation center, Step ST270 is omitted.

The operator OP selects the OK button 128 on the third notification screen 125. Then, the operator OP makes the subject H stand in front of the electronic cassette 10 and adjusts the position and posture of the subject H such that a craniocaudal axis is parallel to the Z-axis or the arms are crossed sideways (Step ST280). Then, the operator OP operates the handle 36 of the first retainer 14 to adjust the height position of the electronic cassette 10 in accordance with the body type of the subject H. Then, the operator OP operates the handle of the second retainer 16 to match the height position of the radiation source 11 with the height position of the electronic cassette 10 (Step ST290). Then, the operator OP operates the console 13 to input the instruction to start the emission of the radiation R to the radiation source control device 12. Then, the radiation R is emitted from the radiation source 11 to the subject H, the electronic cassette 10 detects the radiation R transmitted through the subject H, and a radiographic image is output from the electronic cassette 10 (Step ST300). The radiographic image is transmitted from the electronic cassette 10 to the console 13. Then, the radiographic image is displayed on the touch panel display 55 under the control of the display control unit 72 to be viewed by the operator OP.

As described above, the radiography system 2 comprises the radiation source 11 that emits the radiation R, the electronic cassette 10 that receives the radiation R and detects a radiographic image, the portable first retainer 14 that holds the electronic cassette 10, the string 34 that is attached to the first retainer 14, and the camera 20 that images the string 34. The first retainer 14 includes the lock portion 38 and the movable portion 39 as an inclination change mechanism that can change the inclination of the electronic cassette 10 with respect to the radiation source 11. The string 34 and the camera 20 constitute a first detection mechanism that detects the inclination α of the electronic cassette 10 about the X-axis which intersects the Z-axis and is directed toward the radiation source 11 in a case in which the detection surface 17 for the radiation R in the electronic cassette 10 and the radiation source 11 are disposed to face each other. Since the inclination α of the electronic cassette 10 about the X-axis can be detected by the string 34 and the camera 20, it is possible to reduce the concern that, in a state in which the electronic cassette 10 is inclined about the X-axis, radiography will be performed on the subject in a posture in which the craniocaudal axis is parallel to the Z-axis and a radiography image in which the subject H is obliquely captured will be detected, resulting in a failure in radiography.

The display control unit 72 performs control to display the inclination α of the electronic cassette 10 about the X-axis on the touch panel display 55. Therefore, it is possible to inform the operator OP of the inclination α of the electronic cassette 10 about the X-axis and to prompt the operator OP to consider a technique for reducing the deviation of the inclination of the electronic cassette 10 about the X-axis.

The displacement amount calculation unit 71 calculates the amount of displacement of the movable portion 39 for reducing the deviation of the inclination of the electronic cassette 10 about the X-axis on the basis of the inclination α of the electronic cassette 10 about the X-axis. The display control unit 72 performs control to display the calculated amount of displacement of the movable portion 39 for reducing the deviation of the inclination of the electronic cassette 10 about the X-axis on the touch panel display 55. Therefore, it is possible to inform the operator OP of the amount of displacement of the movable portion 39 for reducing the deviation of the inclination of the electronic cassette 10 about the X-axis. Since the operator OP only needs to adjust the length of the movable portion 39 on the basis of the displayed amount of displacement, it is possible to easily reduce the deviation of the inclination of the electronic cassette 10 about the X-axis.

The first detection mechanism includes the string 34 that hangs down in the direction parallel to the Z-axis and the camera 20 that images the string 34. The image analysis unit 70 analyzes the captured image 75_1 including the string 34 captured by the camera 20 to detect the inclination α of the electronic cassette 10 about the X-axis. The string 34 may be any object as long as it hangs down in the direction parallel to the Z-axis without loosening, and the camera 20 may have sufficient resolution to extract the image of the string 34 using image recognition. Therefore, the inclination α of the electronic cassette 10 about the X-axis can be detected by a relatively inexpensive and simple configuration.

The camera 20 is provided in the radiation source 11. Therefore, it is possible to easily associate the angle of view of the camera 20 with the irradiation field of the radiation R. For example, the line LC that passes through the center of the captured image 75 and is parallel to the Z-axis can be matched with the line that passes through the irradiation center of the radiation R and is parallel to the Z-axis. In addition, in the technology of the present disclosure, "the camera is provided in the radiation source" is a concept including both a case in which the radiation source 11 and the camera 20 are separately provided and the camera 20 is "attached to the radiation source 11" as in the present embodiment and a case in which the camera 20 is "integrally incorporated" in the radiation source 11.

The markers M1 to M4 and the camera 20 are provided as a second detection mechanism for detecting the inclinations β and γ of the electronic cassette 10 about the Y-axis and the Z-axis. It is possible to detect not only the inclination α of the electronic cassette 10 about the X-axis but also the inclinations β and γ of the electronic cassette 10 about the Y-axis and the Z-axis. Therefore, it is possible to reduce the concern that radiography will be performed in a state in which the electronic cassette 10 is inclined about the Y-axis and/or the Z-axis and a radiography image in which the irradiation states of the radiation R are different in the vertical direction and the horizontal direction will be detected, resulting in a failure in radiography.

The display control unit 72 performs control to display the inclinations β and γ of the electronic cassette 10 about the Y-axis and the Z-axis on the touch panel display 55. Therefore, it is possible to inform the operator OP of the inclinations β and γ of the electronic cassette 10 about the Y-axis and the Z-axis and to prompt the operator OP to consider a technique for reducing the deviation of the inclinations of the electronic cassette 10 about the Y-axis and the Z-axis.

The displacement amount calculation unit 71 calculates the amount of displacement of the movable portion 39 for reducing the deviation of the inclination of the electronic cassette 10 about the Y-axis on the basis of the inclination β of the electronic cassette 10 about the Y-axis. The display control unit 72 performs control to display the calculated amount of displacement of the movable portion 39 for reducing the deviation of the inclination of the electronic cassette 10 about the Y-axis on the touch panel display 55. Therefore, it is possible to inform the operator OP of the amount of displacement of the movable portion 39 for reducing the deviation of the inclination of the electronic cassette 10 about the Y-axis. Since the operator OP only needs to adjust the length of the movable portion 39 on the basis of the displayed amount of displacement, it is possible to easily reduce the deviation of the inclination of the electronic cassette 10 about the Y-axis.

Figure 18:
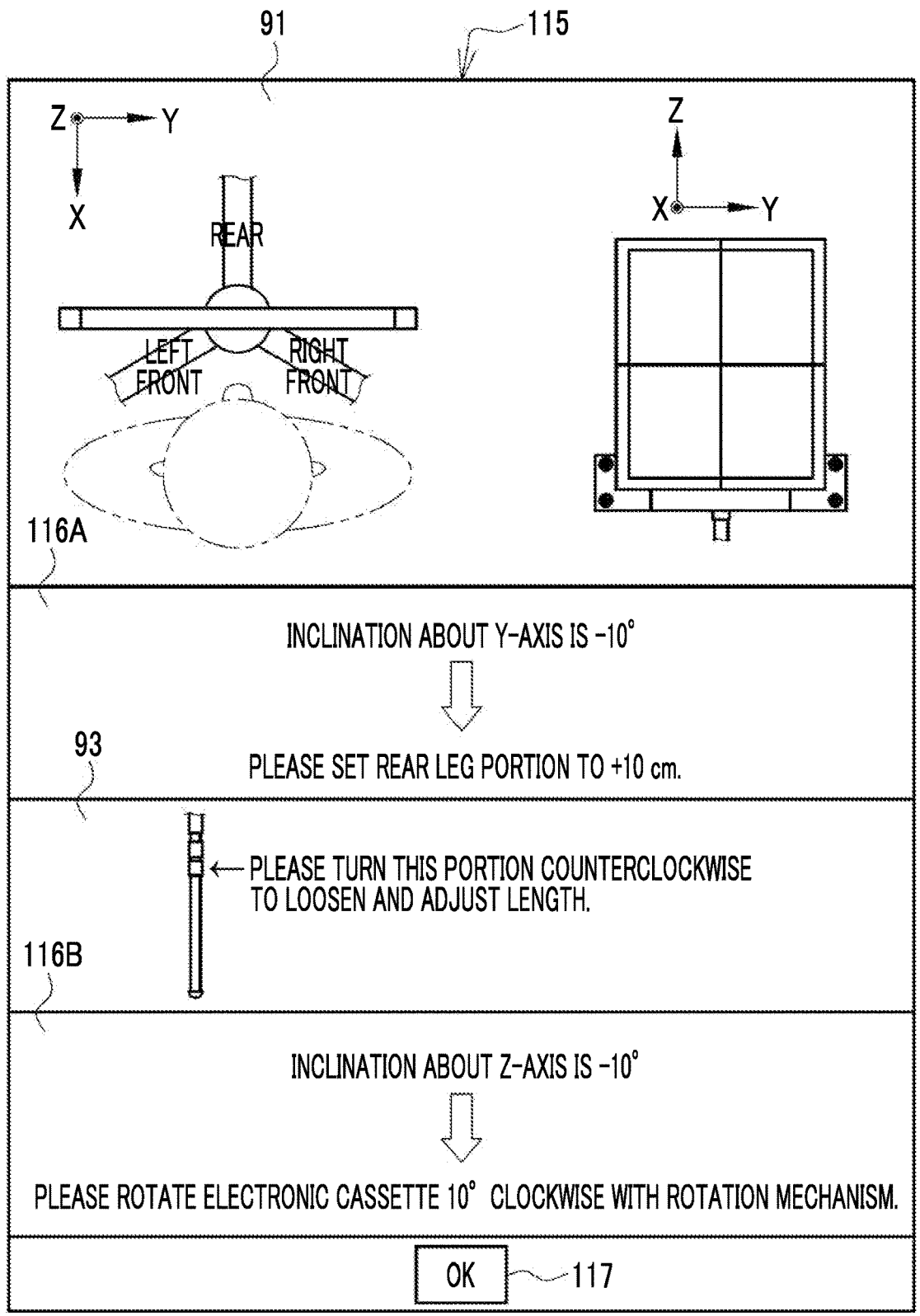
FIG. 18 is a diagram illustrating the second notification screen on which the amount of displacement for reducing the inclination of the electronic cassette about the Z-axis is displayed.

In addition, as the inclination change mechanism that can change the inclination of the electronic cassette 10 about the Z-axis, a rotation mechanism that rotates the electronic cassette 10 about the Z-axis while maintaining the positional relationship between the leg portions 33A to 33C may be provided in the first retainer 14. In this case, the displacement amount calculation unit 71 also calculates the amount of rotation of the rotation mechanism for reducing the deviation of the inclination of the electronic cassette 10 about the Z-axis on the basis of the inclination γ of the electronic cassette 10 about the Z-axis, in addition to the amount of displacement of the movable portion 39 for reducing the deviation of the inclination of the electronic cassette 10 about the Y-axis. In addition, the display control unit 72 also displays the amount of rotation of the rotation mechanism for reducing the deviation of the inclination of the electronic cassette 10 about the Z-axis on the touch panel display 55, as in a result display region 116B of the second notification screen 115 illustrated in FIG. 18 as an example.

The second detection mechanism includes the four markers M1 to M4 provided in the first retainer 14 and the camera 20 that images the markers M1 to M4. The image analysis unit 70 analyzes the captured image 75_2 of the camera 20 to detect the inclinations β and γ of the electronic cassette 10 about the Y-axis and the Z-axis. Therefore, it is possible to detect the inclinations β and γ of the electronic cassette 10 about the Y-axis and the Z-axis with a relatively inexpensive and simple configuration.

The image analysis unit 70 analyzes the captured image 75_3 from the camera 20 and detects the SID which is the distance from the generation point of the radiation R to the detection surface 17 of the electronic cassette 10 and the deviation Δ from the irradiation center which is the position of the electronic cassette 10 with respect to the irradiation center of the radiation R in the YZ plane configured by the Y-axis and the Z-axis. Therefore, the SID can be set to the value associated with the imaging menu, and the deviation Δ from the irradiation center can be reduced. In addition, it is possible to reduce the concern that radiography will fail.

The first retainer 14 includes the holder 30 to which the electronic cassette 10 is attached and three leg portions 33A to 33C that support the holder 30. As described above, since the first retainer 14 has a very simple configuration, it can be easily carried into an imaging site and can be easily installed on the installation surface 15 at the imaging site. In addition, the first retainer 14 is not limited to the illustrated tripod, but may be, for example, a tetrapod or a pentapod. That is, the number of leg portions 33 may be four or more.

The markers M1 to M4 are provided in the holder 30. Therefore, it is possible to prevent the markers M1 to M4 from being included in the radiographic image. Further, in a case in which the markers M1 to M4 are provided at the position of the holder 30 where the markers M1 to M4 are not hidden by the subject H standing in front of the electronic cassette 10, it is possible to adjust the position and posture of the electronic cassette 10 with respect to the radiation source 11 after the subject H is placed in front of the electronic cassette 10. In addition, as in the case in which "the camera is provided in the radiation source", in the technology of the present disclosure, "the markers are provided in the holder" is a concept including both a case in which the holder 30 and the markers M1 to M4 are provided separately and the markers M1 to M4 are attached to the holder 30 as in this embodiment and a case in which the markers M1 to M4 are "integrally incorporated" into the holder 30.

Figure 19:
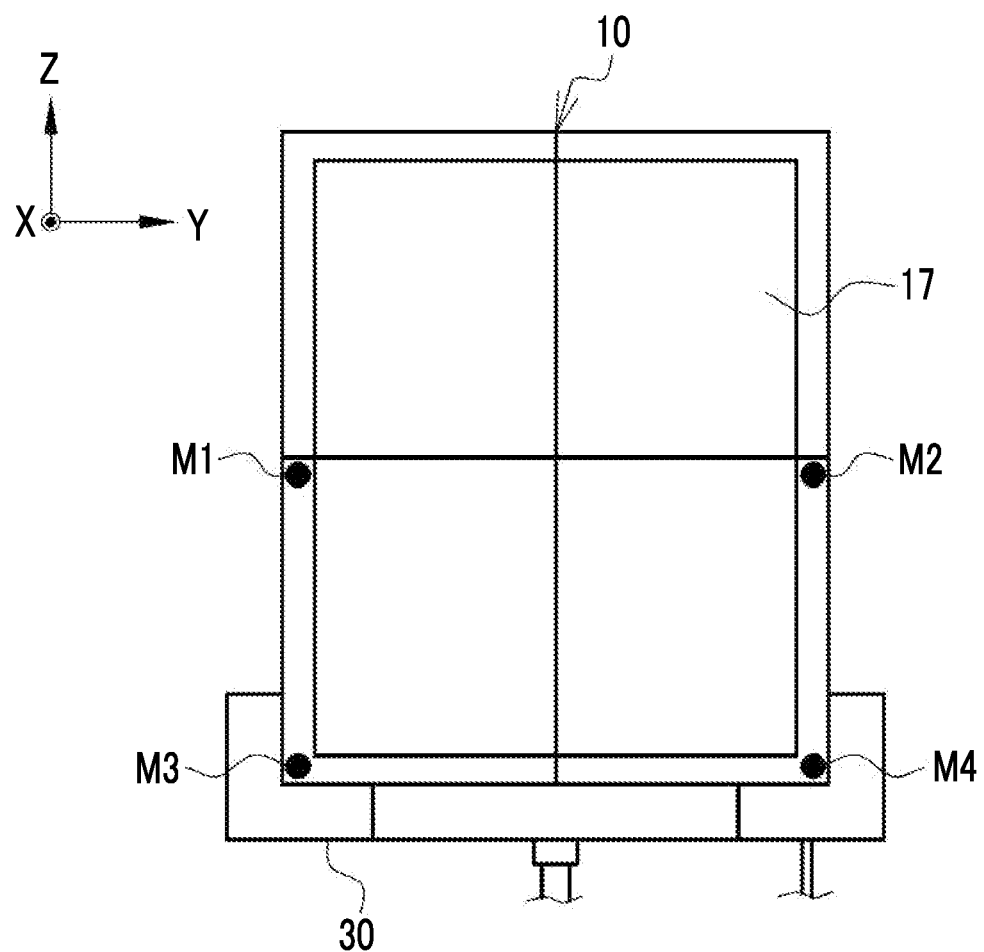
FIG. 19 is a diagram illustrating an example in which markers are provided in the electronic cassette.

Further, for example, as illustrated in FIG. 19, the markers M1 to M4 may be provided in the electronic cassette 10. However, in this case, it is preferable to provide the markers M1 to M4 while avoiding the detection surface 17 of the radiation R in order to prevent the markers M1 to M4 from being included in the radiographic image.

The first retainer 14 includes the fixing mechanism 45 that fixes the positional relationship between the holder 30 and the leg portions 33A to 33C. Therefore, the positional relationship between the holder 30 and the leg portions 33A to 33C can always be fixed to the state illustrated in FIG. 3. In a case in which the subject H stands in front of the electronic cassette 10, the leg portions 33A to 33C do not get in the way. Further, the displacement amount calculation tables 85 and 110 can be created on the premise that the positional relationship between the holder 30 and the leg portions 33A to 33C is fixed, and the amount of displacement of the movable portion 39 can be easily calculated with reference to the displacement amount calculation tables 85 and 110.

Second Embodiment

In the first embodiment, the string 34 and the camera 20 have been described as an example of the first detection mechanism, but the present disclosure is not limited thereto. In a second embodiment, an acceleration sensor 130 is used as the first detection mechanism.

Figure 20:
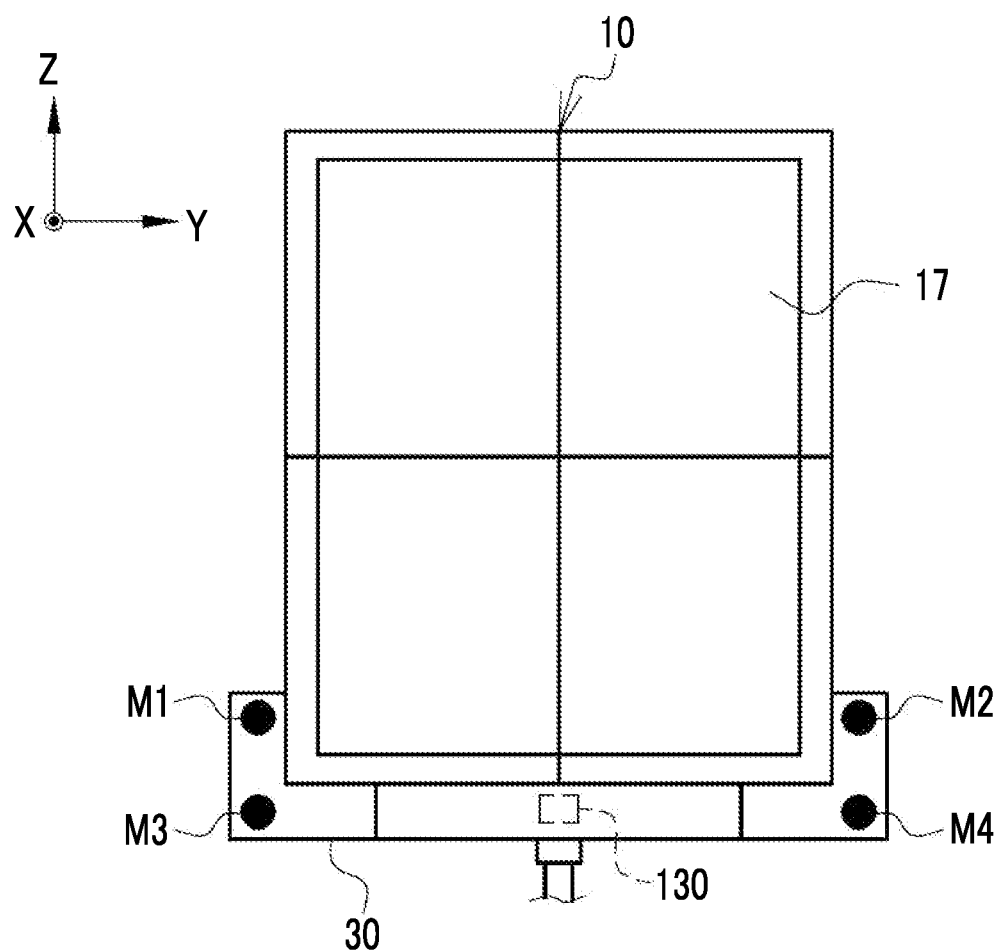
FIG. 20 is a diagram illustrating a second embodiment in which an acceleration sensor is provided as a first detection mechanism.

For example, as illustrated in FIG. 20, the acceleration sensor 130 is provided in a central portion of the holder 30 of the first retainer 14 according to the second embodiment. The acceleration sensor 130 is preset to output gravitational acceleration g as a measurement result 136 (see FIG. 21) in a case in which the inclination α of the electronic cassette 10 about the X-axis is=0°.

Figure 21:
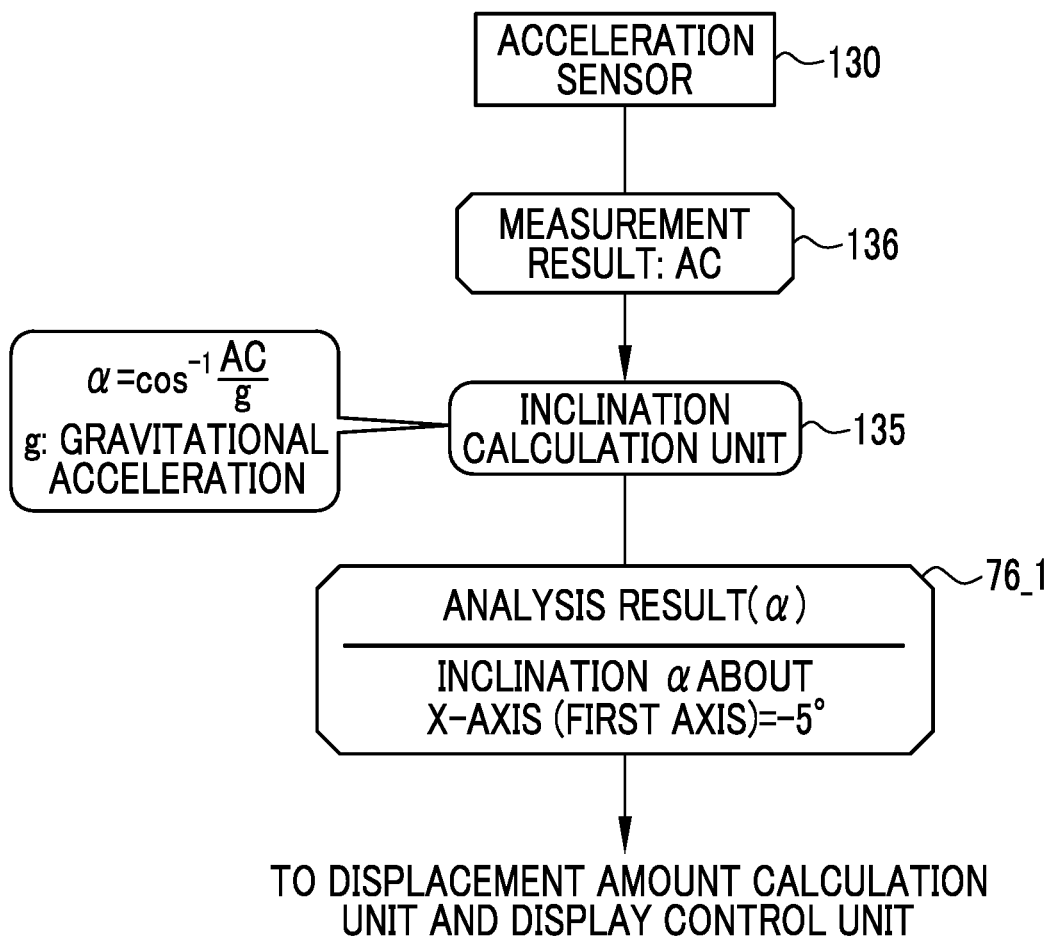
FIG. 21 is a diagram illustrating a processing unit of a CPU of a console according to the second embodiment.

For example, as illustrated in FIG. 21, in addition to the units 70 to 72 according to the first embodiment, an inclination calculation unit 135 is constructed in the CPU 58 of the console 13 according to the second embodiment. The measurement result 136 from the acceleration sensor 130 is input to the inclination calculation unit 135. In a case in which the measurement result 136 is AC, the inclination calculation unit 135 calculates the inclination α of the electronic cassette 10 about the X-axis using the following Expression (1):

$$\alpha = \cos^{-1}(AC/g) \qquad (1).$$

The inclination calculation unit 135 outputs an analysis result 76_1 including the calculated inclination α of the electronic cassette 10 about the X-axis to the displacement amount calculation unit 71 and the display control unit 72.

As described above, in the second embodiment, the first detection mechanism includes the acceleration sensor 130. The inclination calculation unit 135 detects the inclination α of the electronic cassette 10 about the X-axis on the basis of the measurement result 136 of the acceleration sensor 130. The inclination α of the electronic cassette 10 about the X-axis can be detected by a configuration including only the acceleration sensor 130 which is cheaper and simpler than the string 34 and the camera 20. In addition, the acceleration sensor 130 may be provided in the electronic cassette 10 instead of the holder 30.

The center pole 31 may be moved up and down using an actuator such as a motor. In this case, the center pole 31 may be remotely operated by a remote controller to be moved up and down. Not only the center pole 31 of the first retainer 14 but also the center pole of the second retainer 16 may be moved up and down using an actuator, such as a motor, and may be remotely operated by a remote controller to be moved up and down. In addition, the first retainer 14 and the second retainer 16 may be connected such that they can communicate with each other, and the center pole of the second retainer 16 may be moved up and down in operative association with the vertical movement of the center pole 31 of the first retainer 14.

The movable portion 39 may be expanded and contracted using an actuator, such as a motor. In addition, the movable portion 39 may be automatically expanded and contracted according to the amount of displacement calculated by the displacement amount calculation unit 71 without the help of the operator OP. In this case, it is not necessary to display the inclination of the electronic cassette 10 and the amount of displacement of the movable portion 39 for reducing the deviation of the inclination of the electronic cassette 10 on the touch panel display 55.

For example, the calculation of the inclinations β and γ of the electronic cassette 10 about the Y-axis and the Z-axis may be performed first, and the calculation of the inclination α of the electronic cassette 10 about the X-axis may be performed later.

The fixing mechanism for fixing the positional relationship between the holder 30 and the leg portions 33 is not limited to the fixing mechanism 45 (click stop mechanism) given as an example in the first embodiment. A fixing mechanism which fixes the holder 30 and the leg portions 33 not to be rotatable in the positional relationship illustrated in FIG. 3 may be used. In addition, the leg portions 33 may be configured to be freely rotatable with respect to the main body portion 32, and markers may be attached to portions of the main body portion 32 having the positional relationship illustrated in FIG. 3.

At least three markers may constitute the second detection mechanism. Therefore, the number of markers may be five or more. In a case in which the position and posture of the electronic cassette 10 with respect to the radiation source 11 are adjusted after the subject H stands in front of the electronic cassette 10, for example, the inclination α of the electronic cassette 10 about the X-axis may be detected using at least three markers that are not hidden by the subject H among a plurality of markers.

The string 34 may be suspended from the electronic cassette 10. Assuming that the string 34 sways due to wind or the like, a mechanism for suppressing the sway of the string 34 may be provided. In addition, the markers constituting the second detection mechanism may be printed on the electronic cassette 10 or the holder 30.

The electronic cassette is given as an example of the radiographic image detector. However, the present disclosure is not limited thereto. A film cassette or an imaging plate (IP) cassette may be used.

In each of the above-described embodiments, the aspect in which various screens, such as the first notification screen 90, the second notification screen 115, and the third notification screen 125, are displayed on the touch panel display 55 of the console 13, which is a display, under the control of the display control unit 72 of the CPU 58 of the console 13 has been described as an example. However, the present disclosure is not limited thereto. Screen data of various screens, such as the first notification screen 90, the second notification screen 115, and the third notification screen 125, may be generated by the console 13. Then, the generated screen data may be transmitted from the console 13 to another external device having a display, for example, a smart phone owned by the operator OP. In this case, a touch panel display of the smart phone is an example of a "display" according to the technology of the present disclosure.

In each of the above-described embodiments, for example, the following various processors can be used as the hardware structure of processing units performing various processes, such as the image analysis unit 70, the displacement amount calculation unit 71, the display control unit 72, and the inclination calculation unit 135. The various processors include, for example, the CPU 58 which is a general-purpose processor executing software (operation program 60) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of ASICs and/or a combination of an ASIC and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by using one or more of the various processors as a hardware structure.

Furthermore, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other. In addition, the present disclosure is not limited to each of the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, in the content described and illustrated above, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference herein to the same extent as each individual document, each patent application, and each technical standard are specifically and individually stated to be incorporated by reference.

What is claimed is:

1. A radiography system comprising:
a radiation source that emits radiation;
a radiographic image detector that receives the radiation and detects a radiographic image;
a portable retainer that holds the radiographic image detector and includes an inclination change mechanism which is configured to change an inclination of the radiographic image detector with respect to the radiation source; and
a first detection mechanism that detects an inclination of the radiographic image detector about a first axis which intersects a vertical axis and which is directed toward the radiation source in a case in which a detection surface for the radiation in the radiographic image detector and the radiation source are disposed to face each other,
wherein the radiography system further comprises a first processor,
wherein the first detection mechanism comprises a string that hangs down in a direction parallel to the vertical axis and a first camera that images the string,
wherein the first processor analyzes an image including the string captured by the first camera to detect the inclination of the radiographic image detector about the first axis, and
wherein the inclination change mechanism comprises a telescopic movable portion and a lock portion configured to secure the movable portion.

2. The radiography system according to claim 1,
wherein the first processor performs control to display the inclination of the radiographic image detector about the first axis on a display.

3. The radiography system according to claim 2,
wherein the first processor calculates an amount of displacement of the inclination change mechanism for reducing deviation of the inclination of the radiographic image detector about the first axis on the basis of the inclination of the radiographic image detector about the first axis and performs control to display the calculated amount of displacement on the display.

4. The radiography system according to claim 2,
wherein the first detection mechanism includes an acceleration sensor, and
the first processor detects the inclination of the radiographic image detector about the first axis on the basis of a measurement result of the acceleration sensor.

5. The radiography system according to claim 1,
wherein the first camera is provided in the radiation source.

6. The radiography system according to claim 1, further comprising:
a second detection mechanism that detects an inclination of the radiographic image detector about at least one of the vertical axis or a second axis which intersects the vertical axis and the first axis,
wherein the second detection mechanism includes at least three markers that are provided in the radiographic image detector or the retainer, and a second camera that images the markers.

7. The radiography system according to claim 6, further comprising:
a second processor,
wherein the second processor performs control to display the inclination of the radiographic image detector about the at least one of the vertical axis or the second axis on a display.

8. The radiography system according to claim 7,
wherein the second processor calculates an amount of displacement of the inclination change mechanism for reducing deviation of the inclination of the radiographic image detector about the at least one of the vertical axis or the second axis on the basis of the inclination of the radiographic image detector about the at least one of the vertical axis or the second axis and performs control to display the calculated amount of displacement on the display.

9. The radiography system according to claim 7,
wherein the second processor analyzes an image captured by the second camera to detect the inclination of the radiographic image detector about the at least one of the vertical axis or the second axis.

10. The radiography system according to claim 9,
wherein the second processor analyzes the image captured by the second camera to further detect a distance from a generation point of the radiation to the detection surface of the radiographic image detector and a position of the radiographic image detector with respect to an irradiation center of the radiation in a plane configured by the vertical axis and the second axis.

11. The radiography system according to claim 9,
wherein the second camera is provided in the radiation source.

12. The radiography system according to claim 9,
wherein the retainer includes a holder to which the radiographic image detector is attached and at least three leg portions that support the holder, and
the markers are provided in the holder.

13. The radiography system according to claim 1,
wherein the retainer includes a holder to which the radiographic image detector is attached and at least three leg portions that support the holder.

14. The radiography system according to claim 13,
wherein the retainer includes a fixing mechanism that fixes a positional relationship between the holder and the leg portions, and wherein the fixing mechanism includes a holding portion configured to hold a pole that is connected to the holder, such that the pole is movable up and down, includes a click ball that can project from and retract into the holding portion, and includes a rotating portion that is rotated about the holding portion.

\* \* \* \* \*